US007507760B2

(12) United States Patent
Pajouhesh et al.

(10) Patent No.: US 7,507,760 B2
(45) Date of Patent: Mar. 24, 2009

(54) N-TYPE CALCIUM CHANNEL BLOCKERS

(75) Inventors: Hassan Pajouhesh, Vancouver (CA);
Hossein Pajouhesh, Burnaby (CA);
Yanbing Ding, Vancouver (CA);
Terrance P. Snutch, Vancouver (CA)

(73) Assignee: Neuromed Pharmaceuticals Ltd., Vancouver (CA)

( * ) Notice: Subject to any disclaimer, the term of this patent is extended or adjusted under 35 U.S.C. 154(b) by 422 days.

(21) Appl. No.: 10/763,974

(22) Filed: Jan. 22, 2004

(65) Prior Publication Data

US 2005/0165065 A1 Jul. 28, 2005

(51) Int. Cl.
*A61K 31/40* (2006.01)
*C07D 207/14* (2006.01)
(52) U.S. Cl. .................... 514/426; 548/557
(58) Field of Classification Search ........... 548/441, 548/557; 514/426
See application file for complete search history.

(56) References Cited

U.S. PATENT DOCUMENTS

| 3,424,762 | A |  | 1/1969 | Helsley |  |
| 4,785,119 | A |  | 11/1988 | Hojo et al. | 548/557 |
| 5,428,038 | A |  | 6/1995 | Chatterjee et al. | 514/253 |
| 5,624,677 | A |  | 4/1997 | El-Rashidy et al. | 424/435 |
| 5,646,149 | A |  | 7/1997 | Hellberg et al. | 514/253 |
| 5,703,071 | A |  | 12/1997 | Itoh et al. | 514/218 |
| 6,011,035 | A |  | 1/2000 | Snutch et al. | 514/231.2 |
| 6,294,533 | B1 |  | 9/2001 | Snutch et al. | 514/231.2 |
| 6,310,059 | B1 |  | 10/2001 | Snutch | 514/222.2 |
| 6,348,600 | B1 |  | 2/2002 | Ono et al. | 548/545 |
| 6,387,897 | B1 |  | 5/2002 | Snutch | 514/231.2 |
| 6,468,998 | B1 | * | 10/2002 | Kuroita et al. | 514/214.03 |

FOREIGN PATENT DOCUMENTS

| GB | 1281188 |  | 7/1972 |
| JP | 08092207 |  | 4/1996 |
| JP | 11100366 |  | 4/1999 |
| WO | WO 98/17625 |  | 4/1998 |
| WO | WO-01/10799 |  | 2/2001 |
| WO | WO 02/20015 A1 | * | 3/2002 |
| WO | WO-2004/056767 |  | 7/2004 |

OTHER PUBLICATIONS

Augustine et al., Annu Rev Neurosci (1987) 10:633-693.
Backonja et al., JAMA (1998) 280:1831-1836.
Bourinet et al., Nature Neuroscience (1999) 2:407-415.
Bowersox, J Pharmacol Exp Ther, (1996) 279:1243-1249.
Caraceni et al., J Pain & Symp Manag (1999) 17:441-445.
Catterall, Annu Rev Cell Dev Biol (2000) 16:521-55.
Cesena and Calcutt, N.A. Neurosci Lett (1999) 262:101-104.
Chaplan et al., J Pharmacol Exp Ther (1994) 269:1117-1123.
Cheng et al., Anesthesiology (2000) 92:1126-1131.
Corruble et al., Tetrahedron: Asymmetry (1997) 8(10): 1519-1523.
Corruble et al., Journal of the American Chemical Society (1997) 119(42): 10042-10048.
Cribbs et al., Circulation Research (1998) 83:103-109.
De Waard et al., (1996) Structural and functional diversity of voltage activated calcium channels. In: Narahashi (ed.) Ion Channels, Plenum Press, NY.
Di Trapani et al., Clin Ter (2000) 151:145-148.
Dooley, Current Opinion in CPNS Investigational Drugs (1999) 1:116-125.
Dubel et al., Proc. Natl. Acad. Sci. USA (1992) 89:5058-5062.
Dunlap et al., Trends Neurosci (1995) 18:89-98.
Field et al., Pain (1999) 80:391-398.
Fujita et al., Neuron (1993) 10:585-598.
Gomora et al., Mol. Pharmacol (2001) 60:1121-1132.
Gould et al., Proc Natl Acad Sci USA (1983) 80:5122-5125.
Grantham et al., Brit J Pharmacol (1944) 111:483-488.
Hatakeyama et al., NeuroReport (2001) 12:2423-2427.
Heading, Curr Opin CPNS Investigational Drugs (1999) 1:153-166.
Houtchens, Multiple Sclerosis (1997) 3:250-253.
Huguenard, Annu Rev Physiol (1996) 58:329-348.
Ino et al., Proc. Natl. Acad. Sci. USA (2001) 98:5323-5328.
Janis and Triggle, In: Calcium Channels: Their Properties, Functions, Regulation and Clinical Relevance (1991) CRC Press, London.
Jones, Eur J Pharmacol (2002) 447:211-225.
Kim et al., Mol Cell Neurosci (2001) 18:235-245.
Kim et al., Neuron (2001) 31:35-45.
King et al., J Biol Chem (1989) 264:5633-5641.
Laird and Gidal, Annal Pharmacotherap (2000) 34:802-807.
Lee et al., Neuroscience (1999) 19:1912-1921.
Magnus, Epilepsia (1999) 40(Suppl 6):S66-S72.
Malmberg and Yaksh, J Neurosci (1994) 14:4882-4890.
Mathur, Seminars in Anesthesia, Perioperative medicine and Pain (2000) 19:67-75.
McCleskey and Schroeder, Cur Topics Membr (1991) 39:295-326.
McRory et al., J Biol Chem (2001) 276:3999-4011.
Mikami et al., Nature (1989) 340:230-233.
Miller, Science (1987) 235:46-52.
Mori et al., Nature (1991) 350:398-402.
Nicholson, Acta Neurol Scand (2000) 101:359-371.
Penn and Paice, Pain (2000) 85:291-296.
Perez-Reyes et al., Nature (1998) 391:896-900.
Perez-Reyes, Physiol Rev (2003) 83:117-161.
Prigent et al., Journal de Chimie Physique et de Physico-Chimie Biologique (1998) 95(2): 401-405.
Ridgeway et al., Pain (2000) 85:287-289.
Rowbotham et al., JAMA (1998) 280:1837-1842.
Saegusa et al., Proc. Natl. Acad. Sci. USA (2000) 97:6132-6137.
Salemme et al., Structure (1997) 5:319-324.
Santi et al., J Neurosci (2002) 22:396-403.
Sather et al., Neuron (1993) 11:291-303.
Sluka, J Pharmacol Exp Ther (1998) 287:232-237.
Snutch, et al., Neuron (1991) 7:45-57.

(Continued)

*Primary Examiner*—Rei-Tsang Shiao
*Assistant Examiner*—Joseph R Kosack
(74) *Attorney, Agent, or Firm*—Morrison & Foerster LLP

(57) ABSTRACT

The invention relates to novel 3-amino pyrrolidine derivatives, as well as methods for modulating calcium channel activity and for treating conditions associated with calcium channel function. In particular, the compounds generally contain at least one benzhydril moiety, and are useful in treating conditions which benefit from blocking calcium ion channels.

20 Claims, 10 Drawing Sheets

OTHER PUBLICATIONS

Soong, et al., Science (1993) 260:1133-1136.
Stea et al., Voltage-gated calcium channels. In: Handbook on Ion Channels. North (ed.) CRC Press, pp. 113-151 (1994).
Stea et al., Proc. Natl. Acad. Sci. USA (1994) 91:10576-10580.
Su et al., J Neurosci (2002) 22:3645-3655.
Taylor et al., Epilepsy Res (1998) 29:233-249.
Tomlinson et al., Neuropharmacology (1993) 32:1117-1126.
Tumilowicz et al., Cancer Res (1970) 30(8):2110-2118.
Vanegas and Schaible, Pain (2000) 85:9-18.
Wade, Organic Chemistry (1987) pp. 333-398, Prentice-Hall, Inc., Englewood Cliffs, New Jersey.
Wang et al., Soc Neurosci Abstr (1998) 24:1626.
Wentworth and Janda, Curr Opin Biotechnol (1998) 9:109-115.
Williams, Science (1992) 257:389-395.
Williams, Neuron (1992) 8:71-84.
Helsley et al., Journal of Medicinal Chemistry (1968) 11(5):1034-1037.
Lavrador et al., Journal of Medicinal Chemistry (2004) 47(27):6864-6874.
International Search Report for PCT/CA2005/000073, mailed on May 16, 2005, 6 pages.
Registry No. 360056-27-5 CAPLUS (2002).
Registry No. 484049-87-8 CAPLUS (2004).

* cited by examiner

| No. | Compound | Name |
|---|---|---|
| P1 | | (R)-N-{1-[6,6-Bis-(4-fluoro-phenyl)-hexanoyl]-pyrrolidin-3-yl}-3,5-di-tert-butyl-4-methoxy-N-methyl-benzamide |
| P2 | | (R)-6,6-Bis-(4-fluoro-phenyl)-hexanoic acid [1-(3,5-di-tert-butyl-4-methoxy-benzoyl)-pyrrolidin-3-yl]-methyl-amide |
| P3 | | (R)-N-(1-Benzhydryl-pyrrolidin-3-yl)-N-methyl-3,3-diphenyl-propionamide |
| P4 | | (S)-N-{1-[6,6-Bis-(4-fluoro-phenyl)-hexanoyl]-pyrrolidin-3-yl}-3,5-di-tert-butyl-4-methoxy-N-methyl-benzamide |
| P5 | | (S)-6,6-Bis-(4-fluoro-phenyl)-hexanoic acid [1-(3,5-di-tert-butyl-4-methoxy-benzoyl)-pyrrolidin-3-yl]-methyl-amide |
| P6 | | (S)-N-(1-Benzhydryl-pyrrolidin-3-yl)-N-methyl-3,3-diphenyl-propionamide |
| P7 | | (R)-N-Methyl-3,3-diphenyl-N-(1-pyridin-4-ylmethyl-pyrrolidin-3-yl)-propionamide |
| P8 | | (R)-N-Methyl-3,3-diphenyl-N-(1-pyridin-3-ylmethyl-pyrrolidin-3-yl)-propionamide |

Figure 1

| No. | Compound | Name |
|---|---|---|
| P9 | 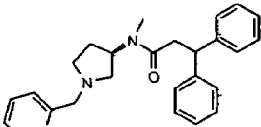 | (R)-N-Methyl-3,3-diphenyl-N-(1-pyridin-2-ylmethyl-pyrrolidin-3-yl)-propionamide |
| P10 | 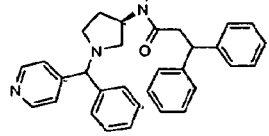 | (R)-N-Methyl-3,3-diphenyl-N-[1-(phenyl-pyridin-4-yl-methyl)-pyrrolidin-3-yl]-propionamide |
| P11 | 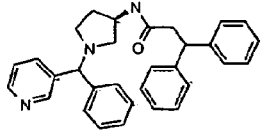 | (R)-N-Methyl-3,3-diphenyl-N-[1-(phenyl-pyridin-3-yl-methyl)-pyrrolidin-3-yl]-propionamide |
| P12 | 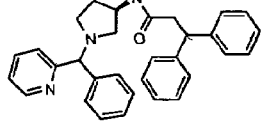 | (R)-N-Methyl-3,3-diphenyl-N-[1-(phenyl-pyridin-2-yl-methyl)-pyrrolidin-3-yl]-propionamide |
| P13 | 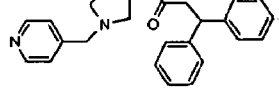 | (S)-N-Methyl-3,3-diphenyl-N-(1-pyridin-4-ylmethyl-pyrrolidin-3-yl)-propionamide |
| P14 | 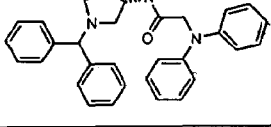 | (S)-N-(1-Benzhydryl-pyrrolidin-3-yl)-2-diphenylamino-N-methyl-acetamide |
| P15 | 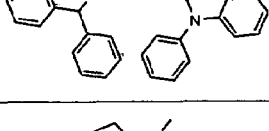 | (S)-2-[(1-Benzhydryl-pyrrolidin-3-yl)-methyl-amino]-N,N-diphenyl-acetamide |
| P16 | 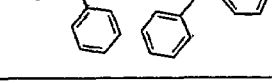 | (S)-3-Benzhydryl-1-(1-benzhydryl-pyrrolidin-3-yl)-1-methyl-urea |

Figure 1

| No. | Compound | Name |
|---|---|---|
| P17 | | (S)-N-Methyl-3,3-diphenyl-N-(1-pyridin-3-ylmethyl-pyrrolidin-3-yl)-propionamide |
| P18 | | (S)-N-Methyl-3,3-diphenyl-N-(1-pyridin-2-ylmethyl-pyrrolidin-3-yl)-propionamide |
| P19 | | (R)-{1-[6,6-Bis-(4-fluoro-phenyl)-hexyl]-pyrrolidin-3-yl}-(3,5-di-tert-butyl-4-methoxy-benzyl)-methyl-amine |
| P20 | | (R)-[6,6-Bis-(4-fluoro-phenyl)-hexyl]-[1-(3,5-di-tert-butyl-4-methoxy-benzyl)-pyrrolidin-3-yl]-methyl-amine |
| P21 | | (S)-{1-[6,6-Bis-(4-fluoro-phenyl)-hexyl]-pyrrolidin-3-yl}-(3,5-di-tert-butyl-4-methoxy-benzyl)-methyl-amine |
| P22 | | (S)-[6,6-Bis-(4-fluoro-phenyl)-hexyl]-[1-(3,5-di-tert-butyl-4-methoxy-benzyl)-pyrrolidin-3-yl]-methyl-amine |
| P23 | | (R)-N-{1-[(4-Chloro-phenyl)-phenyl-methyl]-pyrrolidin-3-yl}-N-methyl-3,3-diphenyl-propionamide |
| P24 | | (S)-N-{1-[(4-Chloro-phenyl)-phenyl-methyl]-pyrrolidin-3-yl}-N-methyl-3,3-diphenyl-propionamide |

Figure 1

| No. | Compound | Name |
|---|---|---|
| P25 | | (R)-N-{1-[(3-Chloro-phenyl)-phenyl-methyl]-pyrrolidin-3-yl}-N-methyl-3,3-diphenyl-propionamide |
| P26 | | (S)-N-{1-[(3-Chloro-phenyl)-phenyl-methyl]-pyrrolidin-3-yl}-N-methyl-3,3-diphenyl-propionamide |
| P27 | | (R)-N-{1-[(2-Chloro-phenyl)-phenyl-methyl]-pyrrolidin-3-yl}-N-methyl-3,3-diphenyl-propionamide |
| P28 | | (S)-N-{1-[(2-Chloro-phenyl)-phenyl-methyl]-pyrrolidin-3-yl}-N-methyl-3,3-diphenyl-propionamide |
| P29 | | (R)-N-{1-[6,6-Bis-(4-fluoro-phenyl)-hexanoyl]-pyrrolidin-3-yl}-3,5-di-tert-butyl-N-methyl-benzamide |
| P30 | | (R)-6,6-Bis-(4-fluoro-phenyl)-hexanoic acid [1-(3,5-di-tert-butyl-benzoyl)-pyrrolidin-3-yl]-methyl-amide |
| P31 | | (S)-N-{1-[6,6-Bis-(4-fluoro-phenyl)-hexanoyl]-pyrrolidin-3-yl}-3,5-di-tert-butyl-N-methyl-benzamide |

Figure 1

| No. | Compound | Name |
|---|---|---|
| P32 | | (S)-6,6-Bis-(4-fluoro-phenyl)-hexanoic acid [1-(3,5-di-tert-butyl-benzoyl)-pyrrolidin-3-yl]-methyl-amide |
| P33 | | (R)-N-{1-[6,6-Bis-(4-fluoro-phenyl)-hexanoyl]-pyrrolidin-3-yl}-4-tert-butyl-N-methyl-benzamide |
| P34 | | (R)-6,6-Bis-(4-fluoro-phenyl)-hexanoic acid [1-(4-tert-butyl-benzoyl)-pyrrolidin-3-yl]-methyl-amide |
| P35 | | (S)-N-{1-[6,6-Bis-(4-fluoro-phenyl)-hexanoyl]-pyrrolidin-3-yl}-4-tert-butyl-N-methyl-benzamide |
| P36 | | (S)-6,6-Bis-(4-fluoro-phenyl)-hexanoic acid [1-(4-tert-butyl-benzoyl)-pyrrolidin-3-yl]-methyl-amide |
| P37 | | (S)-N-Methyl-N-[1-(1-methyl-piperidin-4-ylmethyl)-pyrrolidin-3-yl]-3,3-diphenyl-propionamide |
| P38 | | (S)-N-Methyl-N-[1-(1-methyl-piperidin-3-ylmethyl)-pyrrolidin-3-yl]-3,3-diphenyl-propionamide |
| P39 | | (S)-N-Methyl-N-[1-(1-methyl-piperidin-2-ylmethyl)-pyrrolidin-3-yl]-3,3-diphenyl-propionamide |

Figure 1

| No. | Compound | Name |
|---|---|---|
| P40 | | 4-[6,6-Bis-(4-fluoro-phenyl)-hexanoylamino]-1-(3,5-di-tert-butyl-4-methoxy-benzoyl)-pyrrolidine-2-carboxylic acid ethyl ester |
| P41 | | 4-[6,6-Bis-(4-fluoro-phenyl)-hexanoylamino]-1-(3,5-di-tert-butyl-4-methoxy-benzoyl)-pyrrolidine-2-carboxylic acid |
| P42 | | 1-Benzhydryl-4-(3,3-diphenyl-propionylamino)-pyrrolidine-2-carboxylic acid ethyl ester |
| P43 | | 1-Benzhydryl-4-(3,3-diphenyl-propionylamino)-pyrrolidine-2-carboxylic acid |
| P44 | | N-(1-Benzhydryl-2-oxo-pyrrolidin-3-yl)-3,3-diphenyl-propionamide |
| P45 | | 1-Benzhydryl-3-(1-benzhydryl-2-oxo-pyrrolidin-3-yl)-urea |
| P46 | | N-(1-Benzhydryl-2-oxo-pyrrolidin-3-yl)-2-diphenylamino-acetamide |
| P47 | | 2-(1-Benzhydryl-2-oxo-pyrrolidin-3-ylamino)-N,N-diphenyl-acetamide |

Figure 1

Effect of Compound P2 on Various HVA $Ca^{2+}$ Channels

P/Q-type $IC_{50}$ = 428 ± 140 nM (n=6)

N-type $IC_{50}$ = 46 ± 6 nM (n=5)

L-type $IC_{50}$ >>10 µM (n=5) (estimate :66µM)

N-TYPE CALCIUM CHANNEL BLOCKERS

TECHNICAL FIELD

The invention relates to novel compounds, and methods for modulating calcium channel activity and for treating conditions associated with calcium channel function. More specifically, the invention concerns compounds containing substituted or unsubstituted 3-amino pyrrolidine derivatives.

BACKGROUND ART

The entry of calcium into cells through voltage-gated calcium channels mediates a wide variety of cellular and physiological responses, including excitation-contraction coupling, hormone secretion and gene expression (Miller, R. J., *Science* (1987) 235:46-52; Augustine, G. J., et al., *Annu Rev Neurosci* (1987) 10:633-693). In neurons, calcium channels directly affect membrane potential and contribute to electrical properties such as excitability, repetitive firing patterns and pacemaker activity. Calcium entry further affects neuronal functions by directly regulating calcium-dependent ion channels and modulating the activity of calcium-dependent enzymes such as protein kinase C and calmodulin-dependent protein kinase II. An increase in calcium concentration at the presynaptic nerve terminal triggers the release of neurotransmitter and calcium channels, which also affects neurite outgrowth and growth cone migration in developing neurons.

Calcium channels mediate a variety of normal physiological functions, and are also implicated in a number of human disorders. Examples of calcium-mediated human disorders include but are not limited to congenital migraine, cerebellar ataxia, angina, epilepsy, hypertension, ischemia, and some arrhythmias. The clinical treatment of some of these disorders has been aided by the development of therapeutic calcium channel antagonists (e.g., dihydropyridines, phenylalkyl amines, and benzothiazepines all target L-type calcium channels) (Janis, R. J. and Triggle, D. J., in *Calcium Channels: Their Properties, Functions, Regulation and Clinical Relevance* (1991) CRC Press, London).

Native calcium channels have been classified by their electrophysiological and pharmacological properties into T-, L-, N—, P/Q- and R-types (reviewed in Catterall, W., *Annu Rev Cell Dev Biol* (2000) 16:521-55; Huguenard, J. R., *Annu Rev Physiol* (1996) 58:329-348). T-type (or low voltage-activated) channels describe a broad class of molecules that transiently activate at negative potentials and are highly sensitive to changes in resting potential.

The L-, N— and P/Q-type channels activate at more positive potentials (high voltage-activated), and display diverse kinetics and voltage-dependent properties (Catterall, W., supra; Huguenard, J. R., supra). L-type channels can be distinguished by their sensitivity to several classes of therapeutically useful small organic molecules, including dihydropyridines (DHPs), phenylalkylamines and benzothiazepines. In contrast, N-type and P/Q-type channels are high affinity targets for certain peptide toxins produced by venous spiders and marine snails. N-type channels are blocked by the ω-conopeptides ω-conotoxin GVIA (ω-CTx-GVIA) isolated from *Conus geographus* and ω-conotoxin MVIIA (ω-CTx-MVIIA) isolated from *Conus magus*. On the other hand, P/Q-type channels are resistant to ω-CTx-MVIIA, but are sensitive to the funnel web spider peptide, ω-agatoxin IVA (ω-Aga-IVA). R-type calcium channels. are sensitive to blocking by the tarantula toxin, SNX-482.

Neuronal high voltage-activated calcium channels are composed of a large (>200 kDa) pore-forming $\alpha_1$ subunit that is the target of identified pharmacological agents, a cytoplasmically localized ~50-70 kDa $\beta$ subunit that tightly binds the $\alpha_1$ subunit and modulates channel biophysical properties, and an ~170 kDa $\alpha_2\delta$ subunit (reviewed by Stea, A., et al., *Proc. Natl. Acad. Sci. USA* (1994) 91:10576-10580; Catterall, W., supra). At the molecular level, nine different $\alpha_1$ subunit genes expressed in the nervous system have been identified and shown to encode all of the major classes of native calcium currents (Table 1).

TABLE 1

Classification of Neuronal Calcium Channels

| Native Class | cDNA | Gene Name | ω-AGA IVA | ω-CTx GVIA | ω-CTx MVIIA | dihydropyridines |
|---|---|---|---|---|---|---|
| P/Q-type | $\alpha_{1A}$ | $Ca_v2.1$ | ✓ | — | — | — |
| N-type | $\alpha_{1B}$ | $Ca_v2.2$ | — | ✓ | ✓ | — |
| L-type | $\alpha_{1C}$ | $Ca_v1.2$ | — | — | — | ✓ |
| L-type | $\alpha_{1D}$ | $Ca_v1.3$ | — | — | — | ✓ |
| R-type | $\alpha_{1E}$ | $Ca_v2.3$ | — | — | — | — |
| L-type | $\alpha_{1F}$ | $Ca_v1.4$ | — | — | — | ✓ |
| T-type | $\alpha_{1G}$ | $Ca_v3.1$ | — | — | — | — |
| T-type | $\alpha_{1H}$ | $Ca_v3.2$ | — | — | — | — |
| T-type | $\alpha_{1I}$ | $Ca_v3.3$ | — | — | — | — |

Calcium channels have been shown to mediate the development and maintenance of the neuronal sensitization processes associated with neuropathic pain, and provide attractive targets for the development of analgesic drugs (reviewed in Vanegas, H. and Schaible, H-G., *Pain* (2000) 85:9-18). All of the high-threshold Ca channel types, are expressed in the spinal cord, and the contributions of L-, N and P/Q-types in acute nociception are currently being investigated. In contrast, examination of the functional roles of these channels in more chronic pain conditions strongly indicates a pathophysiological role for the N-type channel (reviewed in Vanegas, H. and Schaible, H-G., supra).

Mutations in calcium channel $\alpha_1$ subunit genes in animals can provide important clues to potential therapeutic targets for pain intervention. Genetically altered mice null for the $\alpha_{1B}$ N-type calcium channel gene have been reported by several independent groups (Ino, M., et al., *Proc. Natl. Acad. Sci. USA* (2001) 98:5323-5328; Kim, C., et al., *Mol Cell Neurosci* (2001) 18:235-245; Kim, D., et al., *Neuron* (2001) 31:35-45; Saegusa, H., et al., *Proc. Natl. Acad. Sci. USA* (2000) 97:6132-6137; Hatakeyama, S., et al., *NeuroReport* (2001) 12:2423-2427). The $\alpha_{1B}$ N-type null mice were viable, fertile and showed normal motor coordination. In one study, peripheral body temperature, blood pressure and heart rate in the N-type gene knock-out mice were all normal (Saegusa, H, et al., supra). In another study, the baroreflex mediated by the sympathetic nervous system was reduced after bilateral carotid occlusion (Ino, M., et al., supra). In another study, mice were examined for other behavioral changes and were found to be normal except for exhibiting significantly lower anxiety-related behaviors (Saegusa, H, et al., supra). These results suggest that the N-type channel may be a potential target for mood disorders as well as pain. In all studies, mice lacking functional N-type channels exhibit marked decreases in the chronic and inflammatory pain responses. In contrast, mice lacking N-type channels generally showed normal acute nociceptive responses.

Two examples of either FDA-approved or investigational drug that act on N-type channel are gabapentin and ziconotide. Gabapentin, 1-(aminomethyl)cyclohexaneacetic acid (Neurontin®), is an anticonvulsant originally found to be active in a number of animal seizure models (Taylor, C. P., et al., *Epilepsy Res* (1998) 29:233-249). Subsequent work has demonstrated that gabapentin is also successful at preventing hyperalgesia in a number of different animal pain models, including chronic constriction injury (CCI), heat hyperalgesia, inflammation, diabetic neuropathy, static and dynamic mechanoallodynia associated with postoperative pain (Taylor, C. P., et al., supra; Cesena, R. M. and Calcutt, N. A. *Neurosci Lett* (1999) 262:101-104; Field, M. J., et al., *Pain* (1999) 80:391-398; Cheng, J-K., et al., *Anesthesiology* (2000) 92:1126-1131; Nicholson, B. *Acta Neurol Scand* (2000) 101:359-371).

While its mechanism of action is incompletely understood, current evidence suggests that gabapentin does not directly interact with GABA receptors in many neuronal systems, but rather modulates the activity of high threshold calcium channels. Gabapentin has been shown to bind to the calcium channel $\alpha_2\delta$ ancillary subunit, although it remains to be determined whether this interaction accounts for its therapeutic effects in neuropathic pain.

In humans, gabapentin exhibits clinically effective anti-hyperalgesic activity against a wide ranging of neuropathic pain conditions. Numerous open label case studies and three large double blind trials suggest gabapentin might be useful in the treatment of pain. Doses ranging from 300-2400 mg/day were studied in treating diabetic neuropathy (Backonja, M., et al., *JAMA* (1998) 280:1831-1836), postherpetic neuralgia (Rowbotham, M., et al., *JAMA* (1998) 280:1837-1842), trigeminal neuralgia, migraine and pain associated with cancer and multiple sclerosis (Di Trapani, G., et al., *Clin Ter* (2000) 151:145-148; Caraceni, A., et al., *J Pain & Symp Manag* (1999) 17:441-445; Houtchens, M. K., *Multiple Sclerosis* (1997) 3:250-253; see also Magnus, L., *Epilepsia* (1999) 40:S66-S72; Laird, M. A. and Gidal, B. E., *Annal Pharmacotherap* (2000) 34:802-807; Nicholson, B, et al., supra).

Ziconotide (Prialt®; SNX-111) is a synthetic analgesic derived from the cone snail peptide *Conus magus* MVIIA that has been shown to reversibly block N-type calcium channels. In a variety of animal models, the selective block of N-type channels via intrathecal administration of Ziconotide significantly depresses the formalin phase 2 response, thermal hyperalgesia, mechanical allodynia and post-surgical pain (Malmberg, A. B. and Yaksh, T. L., *J Neurosci* (1994) 14:4882-4890; Bowersox, S. S., *J Pharmacol Exp Ther,* (1996) 279:1243-1249; Sluka, K. A., *J Pharmacol Exp Ther* (1998) 287:232-237; Wang, Y-X., et al., *Soc Neurosci Abstr* (1998) 24:1626).

Ziconotide has been evaluated in a number of clinical trials via intrathecal administration for the treatment of a variety of conditions, including post-herpetic neuralgia, phantom limb syndrome, HIV-related neuropathic pain and intractable cancer pain (reviewed in Mathur, V. S., *Seminars in Anesthesia, Perioperative medicine and Pain* (2000) 19:67-75). In phase II and III clinical trials with patients unresponsive to intrathecal opiates, Ziconotide has significantly reduced pain scores and in a number of specific instances resulted in relief after many years of continuous pain. Ziconotide is also being examined for the management of severe post-operative pain, as well as for brain damage following stroke and severe head trauma (Heading, C., *Curr Opin CPNS Investigational Drugs* (1999)1:153-166). In two case studies Ziconotide has been further examined for usefulness in the management of intractable spasticity following spinal cord injury in patients unresponsive to baclofen and morphine (Ridgeway, B., et al., *Pain* (2000) 85:287-289). In one instance Ziconotide decreased the spasticity from the severe range to the mild to none range with few side effects. In another patient, Ziconotide also reduced spasticity to the mild range although at the required dosage significant side effects including memory loss, confusion and sedation prevented continuation of the therapy.

T-type calcium channels are involved in various medical conditions. In mice lacking the gene expressing the $\alpha_{1G}$ subunit, resistance to absence seizures was, observed (Kim, et al., supra). Other studies have also implicated the $\alpha_{1H}$ subunit in the development of epilepsy (Su, H., et al., *J Neurosci* (2002) 22:3645-3655). There is strong evidence that some existing anticonvulsant drugs, such as ethosuximide, function through the blockade of T-type channels (Gomora, J. C., et al., *Mol Pharmacol* (2001) 60:1121-1132).

Low voltage-activated calcium channels are highly expressed in tissues of the cardiovascular system. Mibefradil, a calcium channel blocker 10-30-fold selective for T-type over L-type channels, was approved for use in hypertension and angina. It was withdrawn from the market shortly after launch due to interactions with other drugs (Heady, et al., 2001). Growing evidence suggests T-type calcium channels may also be involved in pain. Both mibefradil and ethosuximide have shown anti-hyperalgesic activity in the spinal nerve ligation model of neuropathic pain in rats (Dogrul, et al., 2003).

U.S. Pat. No. 5,646,149 describes calcium channel antagonists of the formula A-Y—B wherein B contains a piperazine or piperidine ring directly linked to Y. An essential component of these molecules is represented by A, which must be an antioxidant; the piperazine or piperidine itself is said to be important. The exemplified compounds contain a benzhydril substituent, based on known calcium channel blockers. U.S. Pat. No. 5,703,071 discloses compounds indicated to be useful in treating ischemic diseases. A mandatory portion of the molecule is a tropolone residue, with substituents such as piperazine derivatives, including their benzhydril derivatives. U.S. Pat. No. 5,428,038 discloses compounds indicated to exhibit a neural protective and antiallergic effect. These compounds are coumarin derivatives which may include derivatives of piperazine and other six-membered heterocycles. A permitted substituent on the heterocycle is diphenylhydroxymethyl. Thus, approaches in the art for various indications which may involve calcium channel blocking activity have employed compounds which incidentally contain piperidine or piperazine moieties substituted with benzhydril but mandate additional substituents to maintain functionality.

Certain compounds containing both benzhydril moieties and piperidine or piperazine are known to be calcium channel antagonists and neuroleptic drugs. For example, Gould, R. J., et al., *Proc Natl Acad Sci USA* (1983) 80:5122-5125 describes antischizophrenic neuroleptic drugs such as lidoflazine, fluspirilene, pimozide, clopimozide, and penfluridol. It has also been shown that fluspirilene binds to sites on L-type calcium channels (King, V. K., et al., *J Biol Chem* (1989) 264:5633-5641), and also blocks N-type calcium current (Grantham, C. J., et al., *Brit J Pharmacol* (1944) 111:483-488). In addition, Lomerizine, as developed by Kanebo K K, is a known calcium channel blocker. However, Lomerizine is not specific for N-type channels. A review of publications concerning Lomerizine is found in Dooley, D., *Current Opinion in CPNS Investigational Drugs* (1999) 1:116-125.

U.S. Pat. Nos. 6,011,035; 6,294,533; 6,310,059; and 6,387,897 describe selective N-type calcium channel blockers that were designed based on the recognition that the combination of a piperazine or piperidine ring coupled through a linker to a benzhydril moiety results in effective calcium channel blocking activity.

GB 1,281,188 describes 1-substituted-3-amidopyrrolidines with analgesic activity. These compounds have single phenyl groups at R and $R^2$.

U.S. Pat. No. 4,785,119 describes a process for synthesizing certain simple 3-aminopyrrolidine compounds which contain phenyl or diphenyl linked to pyrrolidine by alkylene linkers of 1 or 2 carbon in length. These compounds are described as building blocks for construction of useful products in chemical, pharmaceutical, and agricultural industries, in particular for making certain antibacterial products.

U.S. Pat. No. 6,468,998 describes pyrrolidine compounds with 5,$HT_2$ antagonist activity. Some of the compounds contain benzhydril linked to the 3-amino group, but only by C=O.

SUMMARY OF THE INVENTION

The invention relates to novel compounds, and methods for modulating calcium-channel activity and for treating conditions associated with calcium channel function. In particular, the invention relates to benzhydril or partly saturated benzhydril derivatives of 3-substituted pyrrolidine, with substituents which enhance the calcium channel blocking activity of the compounds. The invention also provides methods for using such compounds in treating conditions such as stroke, anxiety, overactive bladder, inflammatory bowel disease, head trauma, migraine, chronic, neuropathic and acute pain, epilepsy, hypertension, cardiac arrhythmias, and other indications associated with calcium metabolism, including synaptic calcium channel-mediated functions. For example, selective N-type calcium channel blockers are particularly useful for treating pain, stroke, anxiety, epilepsy, inflammatory bowel disease and overactive bladder. Selective T-type calcium channel blockers are useful for treating epilepsy, cardiovascular disease and pain. Dual blockers of both N-type and T-type channels would be especially useful for treating epilepsy, stroke and some forms of pain.

In one aspect, the compounds have the formula:

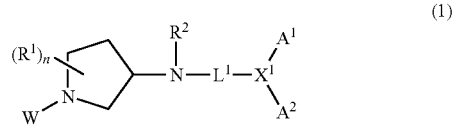
(1)

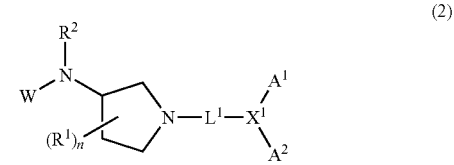
(2)

or the salts thereof, including all stereoisomeric forms thereof, wherein:

$X^1$ is $CR^3$ or N;

W is $L^2$-$A^3$ or $X^1(A^1)(A^2)$;

each of $L^1$ and $L^2$ is a $C_1$-$C_{10}$ optionally substituted alkylene or $C_2$-$C_{10}$ optionally substituted alkenylene, wherein one or more said C is optionally replaced by a heteroatom selected from N, O or S, or further substituted with =O, or both;

each of $A^1$, $A^2$ and $A^3$ is independently an optionally substituted 5-, 6- or 7-membered aliphatic or aromatic ring optionally containing one or more heteroatoms selected from O, N and S, and optionally fused to an additional ring;

$R^1$ and $R^2$ are noninterfering substituents; and $R^3$ is H or a noninterfering, substituent;

with the proviso that if $L^1$ is less than three linking atoms, $R^2$ cannot be hydrogen or $L^1$ must contain a C=O if $R^2$ is hydrogen.

In one aspect, the invention relates to compound of formula 1 and 2, wherein $L^1$ must contain at least three linking atoms and/or C=O if $X^1$ is CH and W is $L^2A^3$. In another aspect, the invention relates to compound of formula 1 and 2, wherein $L^1$ must contain at least three linking atoms if $X^1$ is CH, and W is $L^2\phi$, wherein phenyl is optionally substituted, and wherein $L^2$ contains two linking atoms.

In the above formula 1 and 2, $R^1$ and $R^2$ are noninterfering substituents. $R^3$ may be hydrogen or a noninterfering substituent. In one aspect, the substituents shown in the above formula 1 and 2 are hydrogen. Noninterfering substituents include but are not limited to optionally substituted alkyl (1-10C), alkenyl (2-10C), alkynyl (2-10C), aryl (5-12 ring members), arylalkyl (7-16C) or arylalkenyl (7-16C), each optionally having one or more C, generally 1-4C, or replaced by heteroatoms (N, O and/or S).

Furthermore, each optional substituent (e.g., alkyl, alkenyl, etc.) may include one or more =O. For example, the substituents may form an acyl, amide, or ester linkage with the atom to which it is bound. The substituents include but are not limited to, one or more halo, $CF_3$, CN, OCF, $NO_2$, NO, SO, $SO_2$, $NR_2$, OR, SR, COOR, and/or $CONR_2$, wherein R is H or optionally substituted alkyl, alkenyl, alkynyl, aryl, arylalkyl, or arylalkenyl, as described above. The sulfur atom in such substituents may be oxidized. Furthermore, two substituents may form a 3-7 membered saturated or unsaturated ring, where the ring is optionally substituted and optionally contain one or more heteroatoms (N, S, O). Examples of non-interfering substituents include, but are not limited to, alkyl, alkenyl, alkynyl, aryl, arylalkyl, acyl, =O, halo, OR, $NR_2$, SR, —SOR, —$SO_2R$, —OCOR, —NRCOR, —NRCONR, —NRCOOR, —OCONR, —RCO, —COOR, $SO_2R$, NRSOR, $NRSO_2R$, —$SO_3R$, —$CONR_2$, $SO_2NR_2$, wherein each R is independently H, alkyl (1-8C), CN, $CF_3$, and $NO_2$, and the like.

In the above formula 1 and 2, $R^1$ may be $C_1$-$C_6$ alkyl, $C_2$-$C_6$ alkenyl, or $C_2$-$C_6$ alkynyl, each optionally substituted, and optionally containing one or more heteroatoms selected from O, N and S. $R^1$ may also be an inorganic substituent. Alternatively, two $R^1$ may form =O or =NOH, and n is 0-3. $R^1$ may also be halo, $NO_2$, $SO_2$, SO, NO, =O, =NOH, or COOR wherein R is H or $C_1$-$C_6$ alkyl.

In the above formula 1 and 2, $R^2$ may be H, lower alkyl or lower alkenyl. In one example, $R^2$ is H or methyl.

In the above formula 1 and 2, the linkers $L^1$-$L^2$ are alkylene or alkenylene moieties optionally including 1 or more heteroatoms selected from N, O, and S, and optionally containing noninterfering substituents. The number of members in the chain in the linkers may be 1-10. For example, $L^1$ may be $C_1$-$C_8$ alkylene or $C_1$-$C_8$ alkenylene, and is optionally substituted by =O. In one example, the =O substituent is adjacent to NR² in formula 1, or adjacent to the nitrogen atom on the pyrrolidinyl ring in formula 2.

In the above formula 1 and 2, each of A¹, A² and A³ is independently optionally substituted phenyl, cyclohexyl, 2-, 3- or 4-pyridyl, indolyl, 2- or 4-pyrimidyl, pyridazinyl, benzotriazolyl, or benzimidazolyl. In one example, each of A¹ and A² is substituted with a halo, alkoxy or alkyl. In another example, each of A¹, A² and A³ is independently phenyl, cyclohexyl, pyridyl or pyrimidyl. In yet another example, each of A¹, A² and A³ is phenyl, optionally substituted with a halogen.

In the above formula 1 and 2, W is L²-A³, and A³ is phenyl, cyclohexyl, 2-, 3- or 4-pyridyl, indolyl, 2- or 4-pyrimidyl, pyridazinyl, benzotriazolyl, or benzimidazolyl, each optionally substituted with one or more substituents. In another example, A³ is phenyl or pyridyl optionally substituted with a halo, alkoxy or alkyl.

In another aspect, the invention relates to compounds selected from the group consisting of (R)—N-{1-[6,6-Bis-(4-fluoro-phenyl)-hexanoyl]-pyrrolidin-3-yl}-3,5-di-tert-butyl-4-methoxy-N-methyl-benzamide;
(R)-6,6-Bis-(4-fluoro-phenyl)-hexanoic acid[1-(3,5-di-tert-butyl-4-methoxy-benzoyl)-pyrrolidin-3-yl]-methyl-amide;
(R)-N-(1-Benzhydryl-pyrrolidin-3-yl)-N-methyl-3,3-diphenyl-propionamide;
(S)-N-{1-[6,6-Bis-(4-fluoro-phenyl)-hexanoyl]-pyrrolidin-3-yl}-3,5-di-tert-butyl-4-methoxy-N-methyl-benzamide;
(S)-6,6-Bis-(4-fluoro-phenyl)-hexanoic acid[1-(3,5-di-tert-butyl-4-methoxy-benzoyl)-pyrrolidin-3-yl]-methyl-amide;
(S)-N-(1-Benzhydryl-pyrrolidin-3-yl)-N-methyl-3,3-diphenyl-propionamide;
(R)-N-Methyl-3,3-diphenyl-N-(1-pyridin-4-ylmethyl-pyrrolidin-3-yl)-propionamide;
(R)-N-Methyl-3,3-diphenyl-N-(1-pyridin-3-ylmethyl-pyrrolidin-3-yl)-propionamide;
(R)-N-Methyl-3,3-diphenyl-N-(1-pyridin-2-ylmethyl-pyrrolidin-3-yl)-propionamide;
(R)-N-Methyl-3,3-diphenyl-N-[1-(phenyl-pyridin-4-yl-methyl)-pyrrolidin-3-yl]-propionamide;
(R)-N-Methyl-3,3-diphenyl-N-[1-(phenyl-pyridin-3-yl-methyl)-pyrrolidin-3-yl]-propionamide;
(R)-N-Methyl-3,3-diphenyl-N-[1-(phenyl-pyridin-2-yl-methyl)-pyrrolidin-3-yl]-propionamide;
(S)-N-Methyl-3,3-diphenyl-N-(1-pyridin-4-ylmethyl-pyrrolidin-3-yl)-propionamide;
(S)-N-(1-Benzhydryl-pyrrolidin-3-yl)-2-diphenylamino-N-methyl-acetamide;
(S)-2-[(1-Benzhydryl-pyrrolidin-3-yl)-methyl-amino]-N,N-diphenyl-acetamide;
(S)-3-Benzhydryl-1-(1-benzhydryl-pyrrolidin-3-yl)-1-methyl-urea;
(S)-N-Methyl-3,3-diphenyl-N-(1-pyridin-3-ylmethyl-pyrrolidin-3-yl)-propionamide;
(S)-N-Methyl-3,3-diphenyl-N-(1-pyridin-2-ylmethyl-pyrrolidin-3-yl)-propionamide;
(R)-{1-[6,6-Bis-(4-fluoro-phenyl)-hexyl]-pyrrolidin-3-yl}-(3,5-di-tert-butyl-4-methoxy-benzyl)-methyl-amine;
(R)-[6,6-Bis-(4-fluoro-phenyl)-hexyl]-[1-(3,5-di-tert-butyl-4-methoxy-benzoyl)-pyrrolidin-3-yl]-methyl-amine;
(S)-{1-[6,6-Bis-(4-fluoro-phenyl)-hexyl]-pyrrolidin-3-yl}-(3,5-di-tert-butyl-4-methoxy-benzyl)-methyl-amine;
(S)-[6,6-Bis-(4-fluoro-phenyl)-hexyl]-[1-(3,5-di-tert-butyl-4-methoxy-benzoyl)-pyrrolidin-3-yl]-methyl-amine;
(R)-N-{1-[(4-Chloro-phenyl)-phenyl-methyl]-pyrrolidin-3-yl}-N-methyl-3,3-diphenyl-propionamide;
(S)-N-{1-[(4-Chloro-phenyl)-phenyl-methyl]-pyrrolidin-3-yl}-N-methyl-3,3-diphenyl-propionamide;
(R)-N-{1-[(3-Chloro-phenyl)-phenyl-methyl]-pyrrolidin-3-yl}-N-methyl-3,3-diphenyl-propionamide;
(S)-N-{1-[(3-Chloro-phenyl)-phenyl-methyl]-pyrrolidin-3-yl}-N-methyl-3,3-diphenyl-propionamide;
(R)-N-{1-[(2-Chloro-phenyl)-phenyl-methyl]-pyrrolidin-3-yl}-N-methyl-3,3-diphenyl-propionamide;
(S)-N-{1-[(2-Chloro-phenyl)-phenyl-methyl]-pyrrolidin-3-yl}-N-methyl-3,3-diphenyl-propionamide;
(R)-N-{1-[6,6-Bis-(4-fluoro-phenyl)-hexanoyl]-pyrrolidin-3-yl}-3,5-di-tert-butyl-N-methyl-benzamide;
(R)-6,6-Bis-(4-fluoro-phenyl)-hexanoic acid[1-(3,5-di-tert-butyl-benzoyl)-pyrrolidin-3-yl]-methyl-amide;
(S)-N-{1-[6,6-Bis-(4-fluoro-phenyl)-hexanoyl]-pyrrolidin-3-yl}-3,5-di-tert-butyl-N-methyl-benzamide;
(S)-6,6-Bis-(4-fluoro-phenyl)-hexanoic acid[1-(3,5-di-tert-butyl-benzoyl)-pyrrolidin-3-yl]-methyl-amide;
(R)-N-{1-[6,6-Bis-(4-fluoro-phenyl)-hexanoyl]-pyrrolidin-3-yl}-4-tert-butyl-N-methyl-benzamide
(R)-6,6-Bis-(4-fluoro-phenyl)-hexanoic acid[1-(4-tert-butyl-benzoyl)-pyrrolidin-3-yl]-methyl-amide;
(S)-N-{1-[6,6-Bis-(4-fluoro-phenyl)-hexanoyl]-pyrrolidin-3-yl}-4-tert-butyl-N-methyl-benzamide;
(S)-6,6-Bis-(4-fluoro-phenyl)-hexanoic acid[1-(4-tert-butyl-benzoyl)-pyrrolidin-3-yl]-methyl-amide;
(S)-N-Methyl-N-[1-(1-methyl-piperidin-4-ylmethyl)-pyrrolidin-3-yl]-3,3-diphenyl-propionamide;
(S)-N-Methyl-N-[1-(1-methyl-piperidin-3-ylmethyl)-pyrrolidin-3-yl]-3,3-diphenyl-propionamide;
(S)-N-Methyl-N-[1-(1-methyl-piperidin-2-ylmethyl)-pyrrolidin-3-yl]-3,3-diphenyl-propionamide;
4-[6,6-Bis-(4-fluoro-phenyl)-hexanoylamino]-1-(3,5-di-tert-butyl-4-methoxy-benzoyl)-pyrrolidine-2-carboxylic acid ethyl ester;
4-[6,6-Bis-(4-fluoro-phenyl)-hexanoylamino]-1-(3,5-di-tert-butyl-4-methoxy-benzoyl)-pyrrolidine-2-carboxylic acid;
1-Benzhydryl-4-(3,3-diphenyl-propionylamino)-pyrrolidine-2-carboxylic acid ethyl ester;
1-Benzhydryl-4-(3,3-diphenyl-propionylamino)-pyrrolidine-2-carboxylic acid;
N-(1-Benzhydryl-2-oxo-pyrrolidin-3-yl)-3,3-diphenyl-propionamide;
1-Benzhydryl-3-(1-benzhydryl-2-oxo-pyrrolidin-3-yl)-urea;
N-(1-Benzhydryl-2-oxo-pyrrolidin-3-yl)-2-diphenylamino-acetamide; and
2-(1-Benzhydryl-2-oxo-pyrrolidin-3-ylamino)-N,N-diphenyl-acetamide.

In another aspect, the present invention relates to pharmaceutical compositions comprising a compound of formula 1 and 2, and a pharmaceutically acceptable excipient. The compounds of the invention may also be in the form of a salt if appropriate, or in the form of a prodrug.

In particular examples, compounds having formula 1 and 2 contain at least one chiral center. The compounds may be in the form of isolated stereoisomers or mixtures of various stereoisomers, including enantiomeric mixtures, equimolar mixtures of all possible stereoisomers, or various degrees of chiral, or optical purity.

The invention also relates to methods of antagonizing calcium channel activity using the compounds of formulas 1 and 2, thus treating conditions associated with calcium channel activity. For example, compounds for formulas 1 and 2 may be used for treating conditions associated with undesired calcium channel activity. Alternatively, compounds of formulas 1 and 2 may be used to treat a subject that may have normal calcium channel function which nevertheless results in an undesirable physical or metabolic state.

In one aspect, the invention relates to methods for modulating calcium channel activity in a subject, comprising administering a compound of formula 1 and 2, or a pharmaceutical composition thereof, to a subject in need of such treatment. In another aspect, the invention relates to methods for ameliorating pain in a subject, comprising administering a compound of claim 1 or a pharmaceutical composition thereof to a subject in need of such treatment.

Furthermore, the invention relates to combinatorial libraries containing the compounds of formulas 1 and 2. The invention also relates to methods for screening such libraries for members containing particularly potent calcium channel blocking activity, or for members that antagonize one type of such channels specifically.

BRIEF DESCRIPTION OF THE DRAWINGS

FIG. 1 shows the names and structures of illustrative compounds of the invention.

MODES OF CARRYING OUT THE INVENTION

Figure 2:
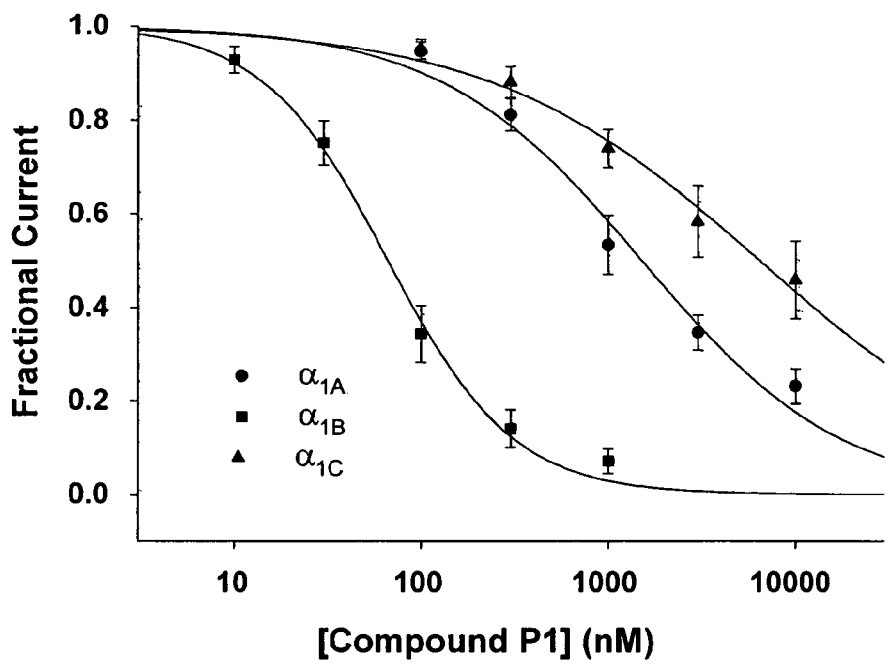
FIG. 2 is a graph showing the selectivity of compound P1 for N—, P/Q- and L-type channels.

The compounds of formulas 1 and 2 exhibit therapeutically desirable effects through their ability to antagonize calcium channel activity. Thus, these compounds are useful for modulating calcium channel activity, and for treating certain conditions. For example, compounds of formula 1 and 2 may be used for treating calcium channel-mediated conditions such as stroke, anxiety, epilepsy, head trauma, migraine and chronic, neuropathic and acute pain, inflammatory bowel disease and overactive bladder. Calcium flux is, also implicated in other neurological disorders such as schizophrenia, depression, drug and alcohol addiction and withdrawal, other psychoses, and certain degenerative disorders. Other conditions treatable with T-type calcium channel blockers include cardiovascular conditions such as hypertension and cardiac arrhythmias. In addition, T-type calcium channels have been implicated in certain types of cancer, diabetes, infertility and sexual dysfunction.

While the compounds of formulas 1 and 2 generally have this activity, the availability of a multiplicity of calcium channel blockers permits a nuanced selection of compounds for particular disorders. Thus, the availability of this class of compounds provides not only a genus of general utility in indications that are affected by calcium channel activity, but also provides a large number of compounds which may be utilized for specific interaction with particular forms of calcium channels. The availability of recombinantly produced calcium channels of the $\alpha_{1A}$-$\alpha_{1I}$ and $\alpha_{1S}$ types set forth above, facilitates this selection process. Dubel, S. J., et al., *Proc. Natl. Acad. Sci. USA* (1992) 89:5058-5062; Fujita, Y., et al., *Neuron* (1993) 10:585-598; Mikami, A., et al., *Nature* (1989) 340:230-233; Mori, Y., et al., *Nature* (1991) 350:398-402; Snutch, T. P., et al., *Neuron* (1991) 7:45-57; Soong, T. W., et al., *Science* (1993) 260:1133-1136; Tomlinson, W. J., et al., *Neuropharmacology* (1993) 32:1117-1126; Williams, M. E., *Science* (1992) 257:389-395; Williams, M. E., *Neuron* (1992) 8:71-84; Perez-Reyes, E., et al., *Nature* (1998) 391:896-900; Cribbs, L. L., et al., *Circulation Research* (1998 83:103-109); Lee, J. H., et al., *Neuroscience* (1999) 19:1912-1921; McRory, J. E., et al., *J Biol Chem* (2001) 276:3999-4011.

There are three distinguishable types of calcium channel inhibition. The first, designated "open channel blockage," is conveniently demonstrated when displayed calcium channels are maintained at an artificially negative resting potential of about −100 mV (as distinguished from the typical endogenous resting maintained potential of about −70 mV). When the displayed channels are abruptly depolarized under these conditions, calcium ions are caused to flow through the channel, and exhibit a peak current flow which then decays. Open channel blocking inhibitors diminish the current exhibited at the peak flow and can also accelerate the rate of current decay.

This type of inhibition is distinguished from a second type of block, referred to herein as, "inactivation inhibition." When maintained at less negative resting potentials, such as the physiologically important potential of −70 mV, a certain percentage of the channels may undergo conformational change, rendering them incapable of being activated (i.e., opened) by the abrupt depolarization. Thus, the peak current due to calcium ion flow will be diminished not because the open channel is blocked, but because some of the channels are unavailable for opening (i.e., inactivated). "Inactivation" type inhibitors increase the percentage of receptors that are in an inactive state.

A third type of inhibition is designated "resting channel block." Resting channel block is the inhibition of the channel that occurs in the absence of membrane depolarization that would normally lead to opening or inactivation. For example, resting channel blockers would diminish the peak current amplitude during the very first depolarization after drug application without additional inhibition during the depolarization.

In addition to a compound's ability to modulate a particular calcium channel, it is desirable that the compound has very low activity with respect to the HERG $K^+$ channel which is expressed in the heart. Compounds that block this channel with high potency may cause fatal side reactions. Thus, a compound that modulates the calcium channel should also not inhibit the HERG $K^+$ channel. Similarly, it would be undesirable for the compound to inhibit cytochrome p450 enzymes since these enzymes are required for drug detoxification. Finally, the compound will be evaluated for calcium ion channel type specificity by comparing its activity among the various types of calcium channels, and specificity for one particular channel type is preferred. The compounds which progress through these tests successfully are then examined in animal models as actual drug candidates.

The Invention Compounds

The invention relates to compounds having the formula:

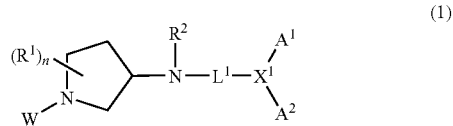

(1)

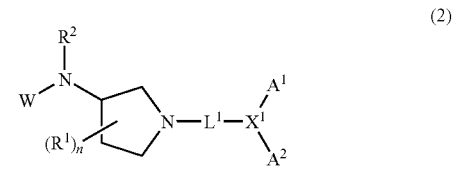

(2)

or the salts thereof, including all stereoisomeric forms thereof, wherein:

$X^1$ is $CR^3$ or N;

W is $L^2$-$A^3$ or $X^1(A^1)(A^2)$;

each of $L^1$ and $L^2$ is a $C_1$-$C_{10}$ optionally substituted alkylene or $C_2$-$C_{10}$ optionally substituted alkenylene, wherein one or more said C is optionally replaced by a heteroatom selected from N, O or S, or further substituted with =O, or both;

each of $A^1$, $A^2$ and $A^3$ is independently an optionally substituted 5-, 6- or 7-membered aliphatic or aromatic ring optionally containing one or more heteroatoms selected from O, N and S, and optionally fused to an additional ring;

$R^1$ and $R^2$ are noninterfering substituents; and $R^3$ is H or a noninterfering substituent;

with the proviso that if $L^1$ is less than three linking atoms, $R^2$ cannot be hydrogen or $L^1$ must contain a C=O if $R^2$ is hydrogen.

In one aspect, each of $A^1$, $A^2$ and $A^3$ (collectively "A") is independently an optionally substituted 5-, 6- or 7-membered aliphatic or aromatic ring, optionally containing one or more heteroatoms selected from O, N and S, and optionally fused to an additional ring. In one example, the rings represented by A are independently optionally substituted phenyl, cyclohexyl, 2-, 3- or 4-pyridyl, indolyl, 2- or 4-pyrimidyl, pyridazinyl, benzotriazolyl or benzimidazolyl. In one example, the rings represented by A are independently phenyl, cyclohexyl, pyridyl, or pyrimidyl. In particular examples, $A^1$, $A^2$ and $A^3$ are independently cyclohexyl or phenyl. Each of these embodiments may optionally be substituted with a group such as optionally substituted alkyl, alkenyl, alkynyl, aryl, O-aryl, O-alkylaryl, O-aroyl, NR-aryl, N-alkylaryl, NR-aroyl, halo, OR, $NR_2$, SR, —OOCR, —NROCR, RCO, —COOR, —$CONR_2$, and/or $SO_2NR_2$, wherein each R is independently H or alkyl (1-8C), and/or by CN, $CF_3$, and/or $NO_2$. In particular embodiments, the optionally substituted alkyl, alkenyl, alkynyl and aryl substituents are independently optionally substituted by similar substituents described above.

The rings represented by A may optionally be substituted with an inorganic substituent or an organic substituent comprising 15 non-hydrogen atoms or less. These substituents include optionally substituted alkyl (1-10C), optionally substituted alkenyl (2-10C), optionally substituted alkynyl (2-10C), an additional aryl moiety (5-12 ring members), arylalkyl, arylalkenyl or arylalkynyl (wherein aryl, alkyl, alkenyl and alkynyl are as defined above). Furthermore, one or more carbons in any of these substituents may be replaced by a heteroatom selected from O, S, and N. Each A may also be independently and optionally substituted with one or more inorganic moieties such as halo, nitro, sulfhydryl, hydroxyl, amino, or forms of OH, SH, or $NH_2$ wherein the H is replaced with optionally substituted organic moieties selected from those listed hereinabove. These moieties may in turn be further substituted, for example, with =O. Among preferred substituents on A are tert-butyl, methoxy, substituted alkoxy, hydroxy and halo.

In another aspect, W is $L^2$-$A^3$ or $X^1(A^1)(A^2)$, wherein $A^1$, $A^2$ and $A^3$ are as described above; $X^1$ is $CR^3$ or N where $R^3$ is hydrogen or a noninterfering substituent; and $L^2$ is a $C_1$-$C_{10}$ optionally substituted alkylene or $C_2$-$C_{10}$ optionally substituted alkenylene, wherein one or more carbons is optionally replaced by a heteroatom selected from N, O or S, or further substituted with =O or both. In one example, the rings represented by A are independently phenyl (Φ), or a partially or fully saturated form thereof ("Cy"). Examples of W include but are not limited to $CH_2\Phi$, $CO\Phi$, $CH\Phi_2$, $CH_2CH_2X^3\Phi$, $COCH_2X^3\Phi$, $CH_2Cy$, $CH_2Cy_2$ and $CHCy\Phi$, wherein $X^3$ is C=O, NR, NCO, S, or O, and where each Φ or Cy is unsubstituted or substituted with 1-3 substituents.

The 1-3 substituents are independently selected from halo, $CF_3$, OCF, lower alkyl (1-6C), lower aryl (6-10C) and arylalkyl (7-16C), each optionally containing 1-4 heteroatoms (N, O, or S) and optionally substituted with inorganic substituents (comprising halo, N, P, O or S. Examples of inorganic substituents include but are not limited to halo, $NO_2$, $NR_2$, OR, SR, COR, COOR, $CONR_2$, NROCR, OOCR where R=H or alkyl (1-8C). Two substituents may form a 3-7 member ring optionally containing a heteroatom (N, S, or O).

In yet another aspect, $R^1$ and $R^2$ are noninterfering substituents. In one example, n is 0-7, preferably 0-2, and most preferably 0-1. If n is 2 or 3, $R^1$ preferably occupies a different position on the pyrrolidine ring. Noninterfering substituents encompassed by $R^1$ include but are not limited to lower alkyl (1-6C), lower alkenyl (2-6C) and lower alkynyl (2-6C), each optionally including one or more heteroatom selected from O, N and S, including substituted forms thereof comprising inorganic substituents such as halo, $NO_2$, $SO_2$, SO, NO and the like. $R^1$ may itself be one of these inorganic substituents. In one example, two $R^1$ together on the same carbon may be =O or =NOH. Examples of $R^2$ include but are not limited to H, lower alkyl, lower alkenyl, and halo, preferably H or lower alkyl, and more preferably H or methyl.

In another aspect, $L^1$ is a linker which spaces the $X^1(A^1)(A^2)$ moiety from either the ring, nitrogen or the nitrogen on the 3-amino substituent on the pyrrolidine. Typically, $L^1$ is an alkylene or alkenylene which is optionally substituted. For example, $L^1$ may be substituted with =O at the carbon adjacent the nitrogen to which $L^1$ is coupled. The alkylene or alkenylene chain may contain 1-10 members, preferably 1-8 members, more preferably 3-6 members. In another example, the alkylene or alkenylene chain is unsubstituted, or contains a single substitution of =O at the carbon adjacent N. This chain may also have one or more carbons replaced by a heteroatom, preferably N or O. In particular embodiments, only a single heteroatom replaces a single carbon.

In another aspect, $L^2$ is a linker as defined in $L^1$, and spaces an $A^3$ ring to either the ring nitrogen or the nitrogen on the 3-amino substituent on the pyrrolidine. In one example, $L^2$ is shorter than $L^1$, and contains 1-4 alkylene or alkenylene members. In another example, $L^2$ contains one alkylene member, which may optionally be substituted. Examples of $L^2$ include but are not limited to $CH_2$ or C=O.

As used herein, the terms "alkyl," "alkenyl" and "alkynyl" include straight-chain, branched-chain and cyclic monovalent substituents, containing only C and H when they are unsubstituted or unless otherwise noted. Examples include methyl, ethyl, isobutyl, cyclohexyl, cyclopentylethyl, 2-propenyl, 3-butynyl, and the like. Typically, the alkyl, alkenyl and alkynyl substituents contain 1-10C (alkyl) or 2-10C (alkenyl or alkynyl). Preferably they contain 1-6C (lower alkyl) or 2-6C (lower alkenyl or lower alkynyl).

Additional examples of optionally substituted alkyl groups include but are not limited to propyl, tert-butyl, and cycloalkyls such as cyclopropyl, cyclobutyl, cyclopentyl, cyclohexyl, cycloheptyl, and the like. Examples of optionally substituted alkenyl groups include but are not limited to allyl, crotyl, 2-pentenyl, 3-hexenyl, 2-cyclopentenyl, 2-cyclohexenyl, 2-cyclopentenylmethyl, 2-cyclohexenylmethyl, and the like. In one embodiment, each of the linkers comprises $C_{1-6}$ alkyl and alkenyl.

As used herein, the terms "heteroalkyl," "heteroalkenyl" and "heteroalkynyl" encompass straight-chain, branched-chain and cyclic monovalent substituents as defined above, and contain one or more O, S or N heteroatoms or combinations thereof within the backbone residue.

As used herein, the term "acyl" encompasses the definitions of alkyl, alkenyl, alkynyl, each of which is coupled to an additional residue through a carbonyl group. As used herein, the term "heteroacyl" includes the related heteroforms of the acyl compounds described.

As used herein, the terms "aromatic" or "aryl" refer to a monocyclic or fused bicyclic moiety such as phenyl or naphthyl. The term "heteroaromatic" refers to monocyclic or fused bicyclic ring systems that contain one or more heteroatoms selected from O, S and N. Any monocyclic or fused ring bicyclic system which has the characteristics of aromaticity in terms of electron distribution throughout the ring system is included in this definition. Examples of aromatic and heteroaromatic systems include but are not limited to pyridyl, pyrimidyl, indolyl, benzimidazolyl, benzotriazolyl, isoquinolyl, quinolyl, benzothiazolyl, benzofuranyl, thienyl, furyl, pyrrolyl, thiazolyl, oxazolyl, imidazolyl and the like. Because tautomers are theoretically possible, phthalimido is also considered aromatic. Typically, the ring systems contain 5-12 ring member atoms. In particular embodiments, the aromatic and heteroaromatic systems contain 5-7 ring member atoms.

Similarly, the terms "arylalkyl" and "heteroarylalkyl" refer to aromatic and heteroaromatic systems which are coupled to another residue through a carbon chain, including substituted or unsubstituted, saturated or unsaturated carbon chains, typically of 1-8C, or the hetero forms thereof. These carbon chains may also include a carbonyl group, thus making them able to provide substituents as an acyl or heteroacyl moiety.

In general, any alkyl, alkenyl, alkynyl, acyl, or aryl group contained in a substituent may itself optionally be substituted by additional substituents. The nature of these substituents is similar to those recited with regard to the primary substituents themselves. For example, an alkyl substituent may optionally be substituted by another substituent including but not limited to alkyl, alkenyl, aryl, amino, alkoxy, and the like.

Examples of halogen include fluorine, chlorine, bromine, iodine, with fluorine and chlorine preferred.

Examples of optionally substituted hydroxyl and thiol groups include optionally substituted alkyloxy or alkylthio (e.g., $C_{1-10}$ alkyl such as methyl, ethyl, propyl, isopropyl, butyl, isobutyl, sec-butyl, tert-butyl, pentyl, cyclopropyl, cyclobutyl, cyclopentyl, cyclohexyl, cycloheptyl, etc.). Optionally substituted hydroxyl and thiol groups also include arylalkyloxy or arylalkylthio (e.g., phenyl-$C_{1-4}$ alkyl, e.g., benzoyl, phenethyl, etc.). Where there are two adjacent hydroxyl or thiol substituents, the heteroatoms may be connected via an alkylene group such as $O(CH_2)_nO$ and $S(CH_2)_nS$ (where n=1-5). Examples include methylenedioxy, ethylenedioxy, etc. Oxides of thio-ether groups such as sulfoxides and sulfones are also included. Other examples of optionally substituted hydroxyl groups are optionally substituted $C_{2-4}$ alkanoyl (e.g., acetyl, propionyl, butyryl, isobutyryl, etc.), $C_{1-4}$ alkylsulfonyl (e.g., methanesulfonyl, ethanesulfonyl, etc.), and an optionally substituted aromatic and heterocyclic carbonyl group including benzoyl, pyridinecarbonyl, etc.

Substituents on optionally substituted amino groups, may bind to each other to form a cyclic amino group (e.g., 5- to 6-membered cyclic amino, etc., such as tetrahydropyrrole, piperazine, piperidine, pyrrolidine, morpholine, thiomorpholine, pyrrole, imidazole, etc.). The cyclic amino group may have a substituent, such as halogen (e.g., fluorine, chlorine, bromine, iodine, etc.), nitro, cyano, hydroxy group, thiol group, amino group, carboxyl group, an optionally halogenated $C_{1-4}$ alkyl (e.g., trifluoromethyl, methyl, ethyl, etc.), an optionally halogenated $C_{1-4}$ alkoxy (e.g., methoxy, ethoxy, trifluoromethoxy, trifluoroethoxy, etc.), $C_{2-4}$ alkanoyl (e.g., acetyl, propionyl, etc.), $C_{1-4}$ alkylsulfonyl (e.g., methanesulfonyl, ethanesulfonyl, etc.). In particular examples, the cyclic amino group is optionally substituted with 1-3 substituents.

An amino group may also be substituted once or twice (to form a secondary or tertiary amine) with a group such as an optionally substituted alkyl group including $C_{1-10}$ alkyl (e.g., methyl, ethyl propyl etc.); an optionally substituted alkenyl group such as allyl, crotyl, 2-pentenyl, 3-hexenyl, etc.; or an optionally substituted cycloalkyl group such as cyclopropyl, cyclobutyl, cyclopentyl, cyclohexyl, cycloheptyl, etc. In particular examples, $C_{1-6}$ alkyl, alkenyl and cycloalkyl are preferred. The amine group may also be optionally substituted with an aromatic or heterocyclic group, aralkyl (e.g., phenyl$C_{1-4}$alkyl) or heteroalkyl. For example, the amino group may optionally be substituted with phenyl, pyridine, phenylmethyl(benzoyl), phenethyl, pyridinylmethyl, pyridinylethyl, etc. The heterocyclic group may be a 5 or 6 membered ring containing 1-4 heteroatoms.

An amino group may be substituted with an optionally substituted $C_{2-4}$ alkanoyl (e.g., acetyl, propionyl, butyryl, isobutyryl etc.), a $C_{1-4}$alkylsulfonyl (e.g., methanesulfonyl, ethanesulfonyl, etc.), or a carbonyl or sulfonyl substituted aromatic or heterocyclic ring, as defined above. Examples of carbonyl or sulfonyl substituted aromatic or heterocyclic rings include but are not limited to benzenesulfonyl, benzoyl, pyridinesulfonyl, or pyridinecarbonyl.

Examples of optionally substituted carbonyl groups, or sulfonyl groups include optionally substituted forms of such groups formed from various hydrocarbyls such as alkyl, alkenyl and 5- to 6-membered monocyclic aromatic group (e.g., phenyl, pyridyl, etc.), as defined above.

The compounds of the invention may have ionizable groups, and may be prepared as, pharmaceutically acceptable salts. These salts may be acid addition salts involving inorganic or organic acids. Alternatively, the salts may be prepared from inorganic or organic bases, particularly where the compounds are acidic. Examples of inorganic bases include but are not limited to alkali metal hydroxides (e.g., sodium hydroxide, potassium hydroxide, etc.), alkaline earth metal hydroxides (e.g., of calcium, magnesium, etc.), and hydroxides of aluminum, ammonium, etc. Examples of organic bases include but are not limited to trimethylamine, triethylamine, pyridine, picoline, ethanolamine, diethanolamine, triethanolamine, dicyclohexylamine, N,N'-dibenzoylethylenediamine, etc. Examples of inorganic acids include hydrochloric acid, hydrobromic acid, nitric acid, sulfuric acid, phosphoric acid, etc. Examples of organic acids include formic acid, oxalic acid, acetic acid, tartaric acid, methanesulfonic acid, benzenesulfonic acid, malic acid, methanesulfonic acid, benzenesulfonic acid, p-toluenesulfonic acid, etc. Also included are salts with basic amino acids such as arginine, lysine, ornithine, etc., and salts with acidic amino acids such as aspartic acid, glutamic acid, etc.

In addition, the compounds of the invention contain one or more chiral centers. The invention includes the isolated stereoisomeric forms, as well as mixtures of stereoisomers in varying degrees of chiral purity. For example, the compounds of the present invention may have R or S configurations at the chiral atom, or mixtures thereof. (See, Wade, Jr., *Organic Chemistry* (1987) pages 333-398, Prentice-Hall, Inc., Englewood Cliffs, N.J.).

Synthesis of the Invention Compounds
The compounds of the invention may be synthesized using conventional methods. Illustrative of such methods are Schemes A, B, C, D, E, F, G and H.
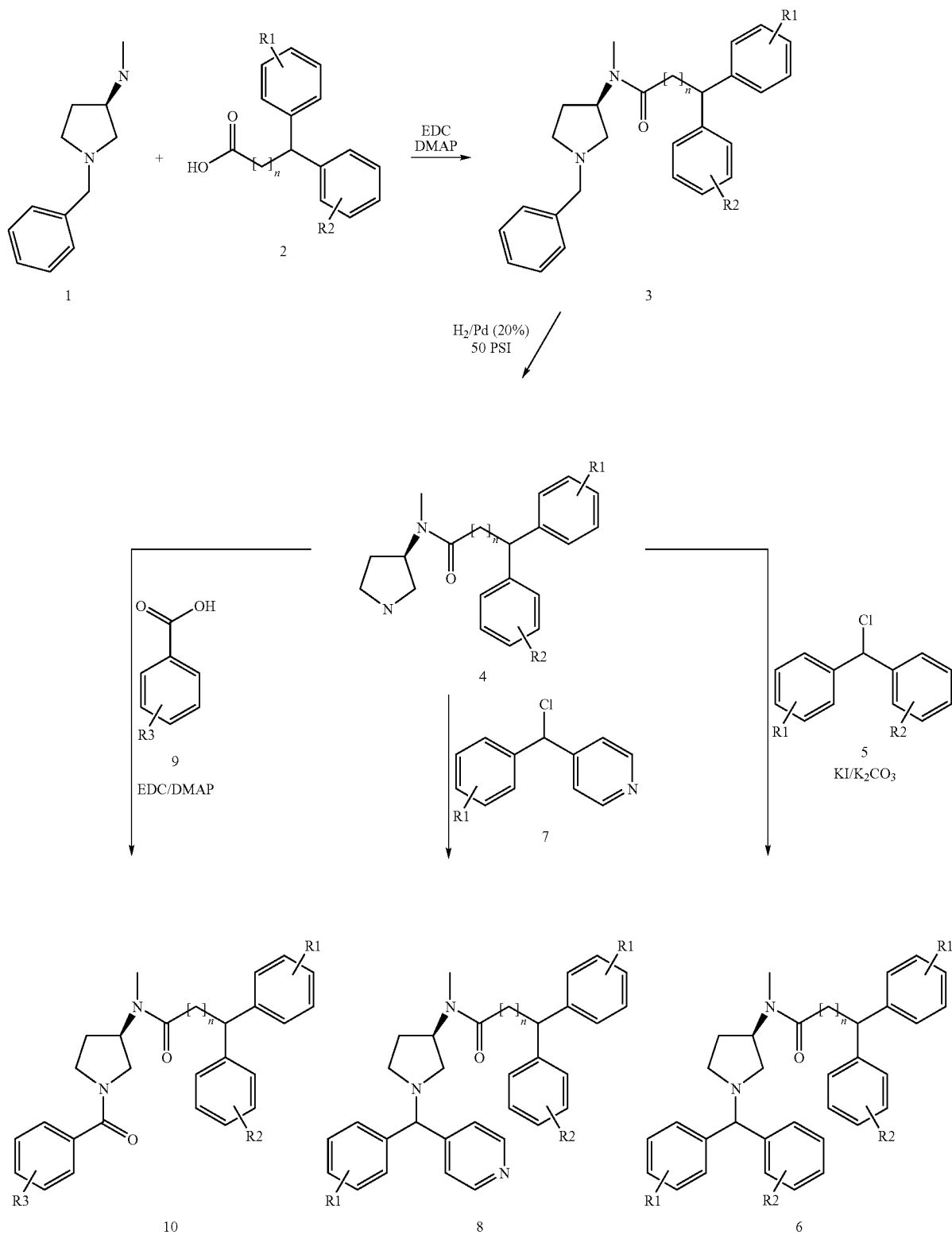
Reaction Scheme A

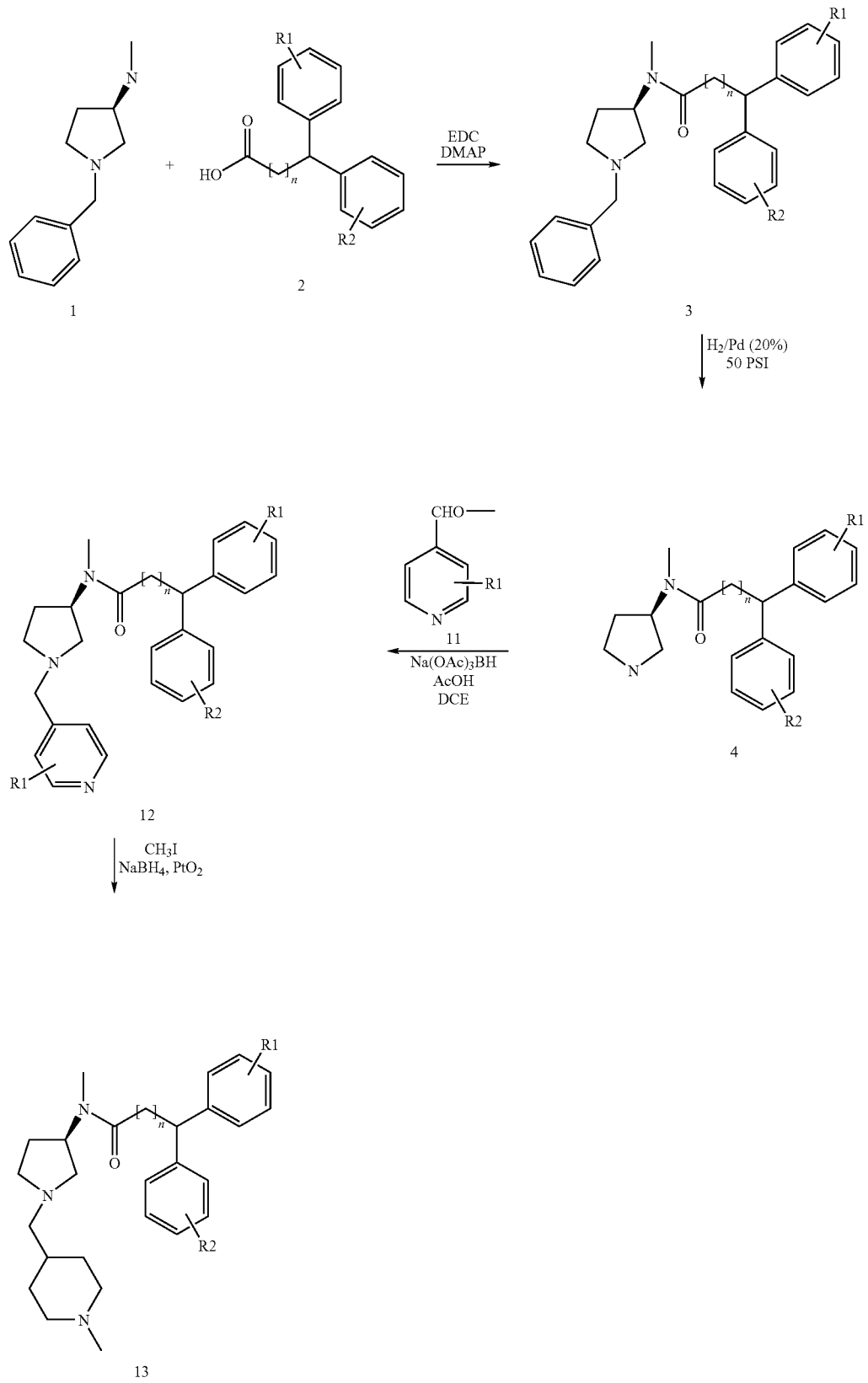

Reaction Scheme C
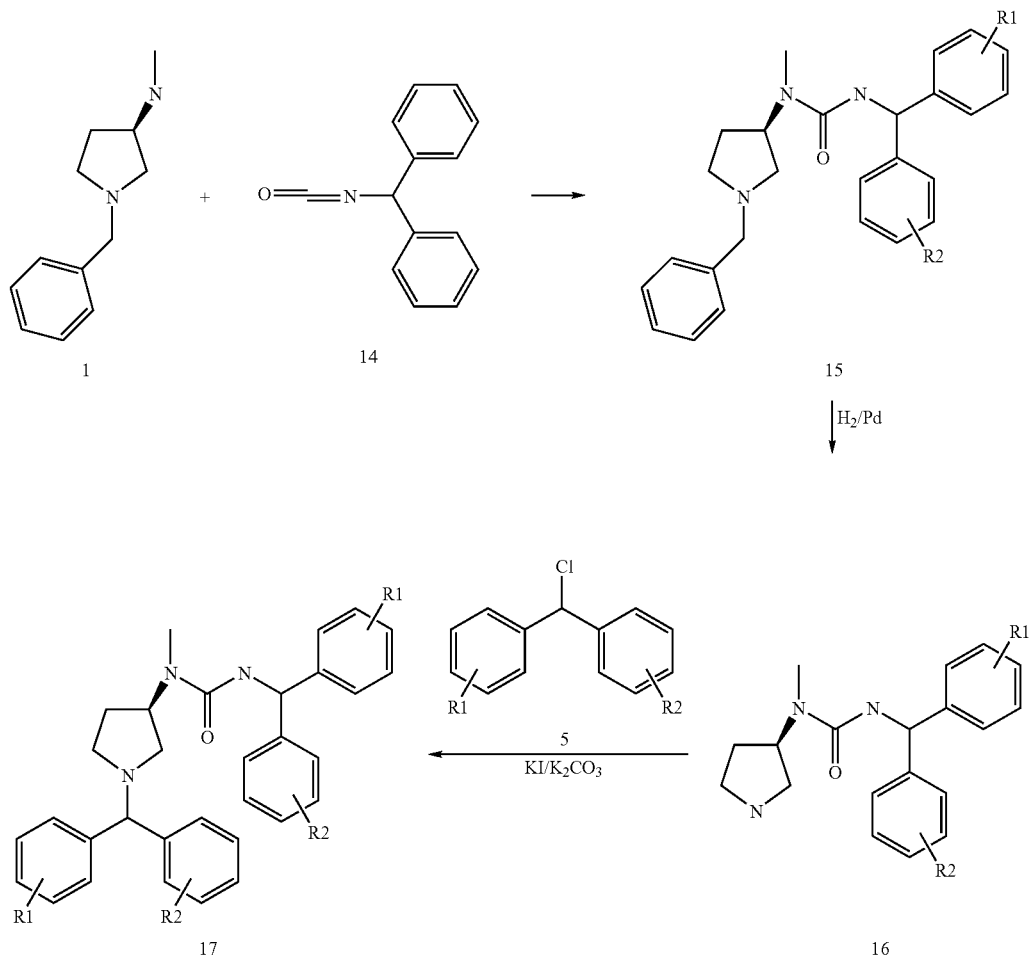
Reaction Scheme D
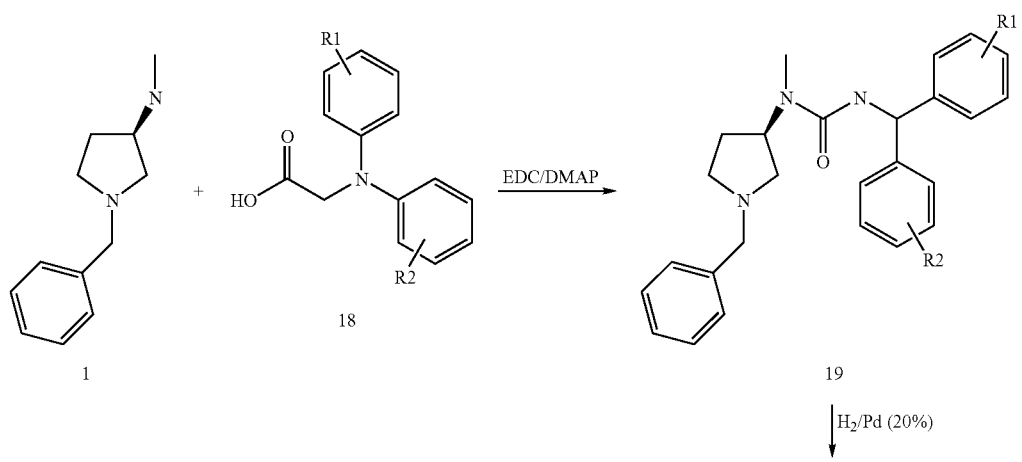

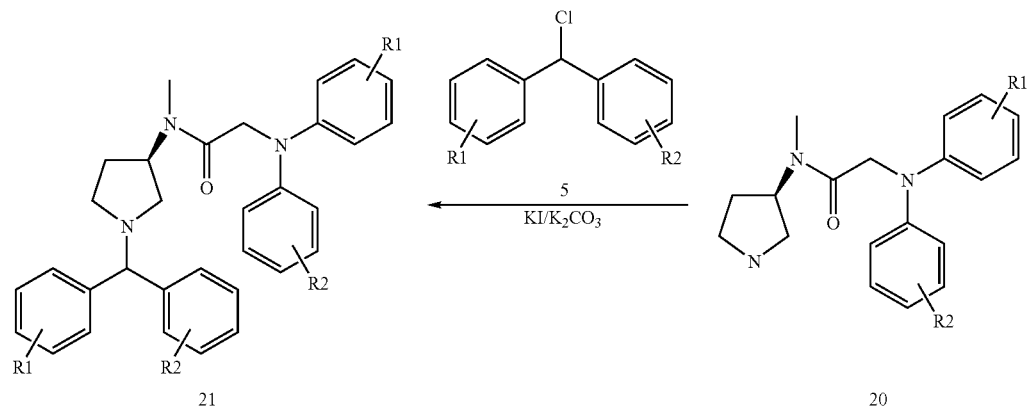
-continued
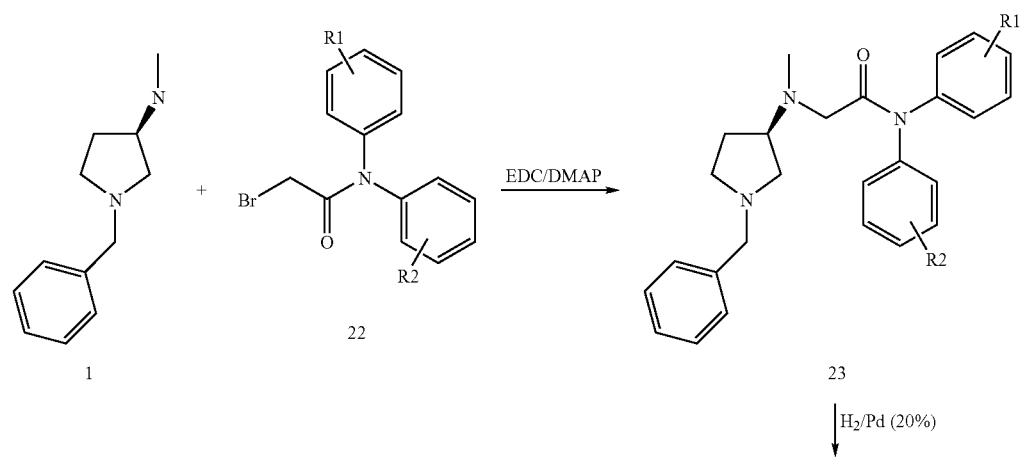
Reaction Scheme E
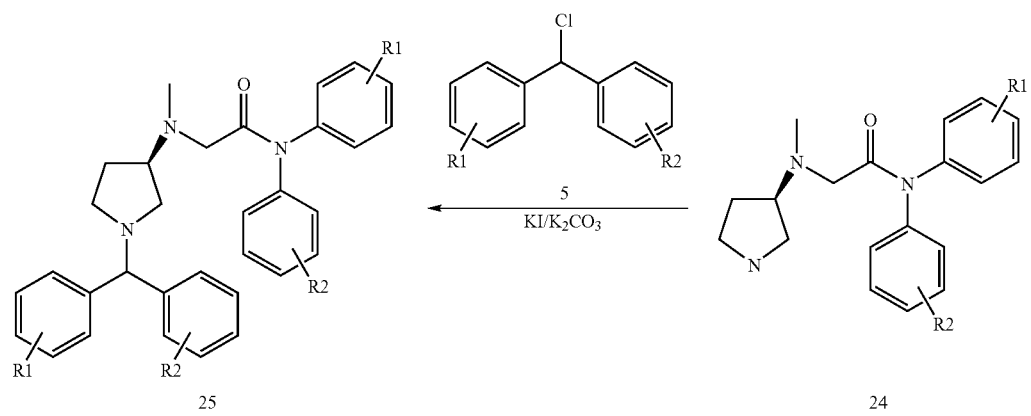

Reaction Scheme F
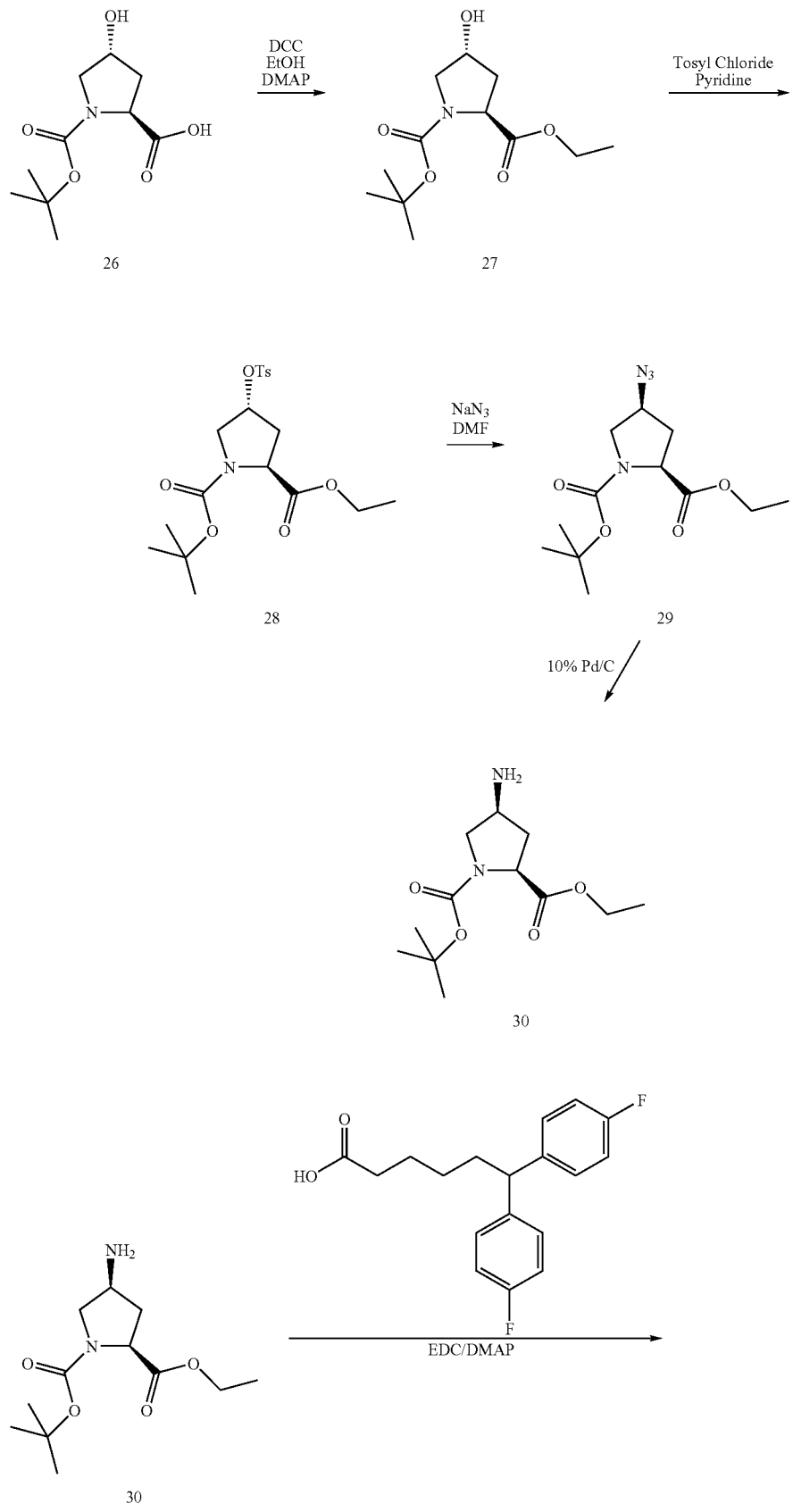

-continued
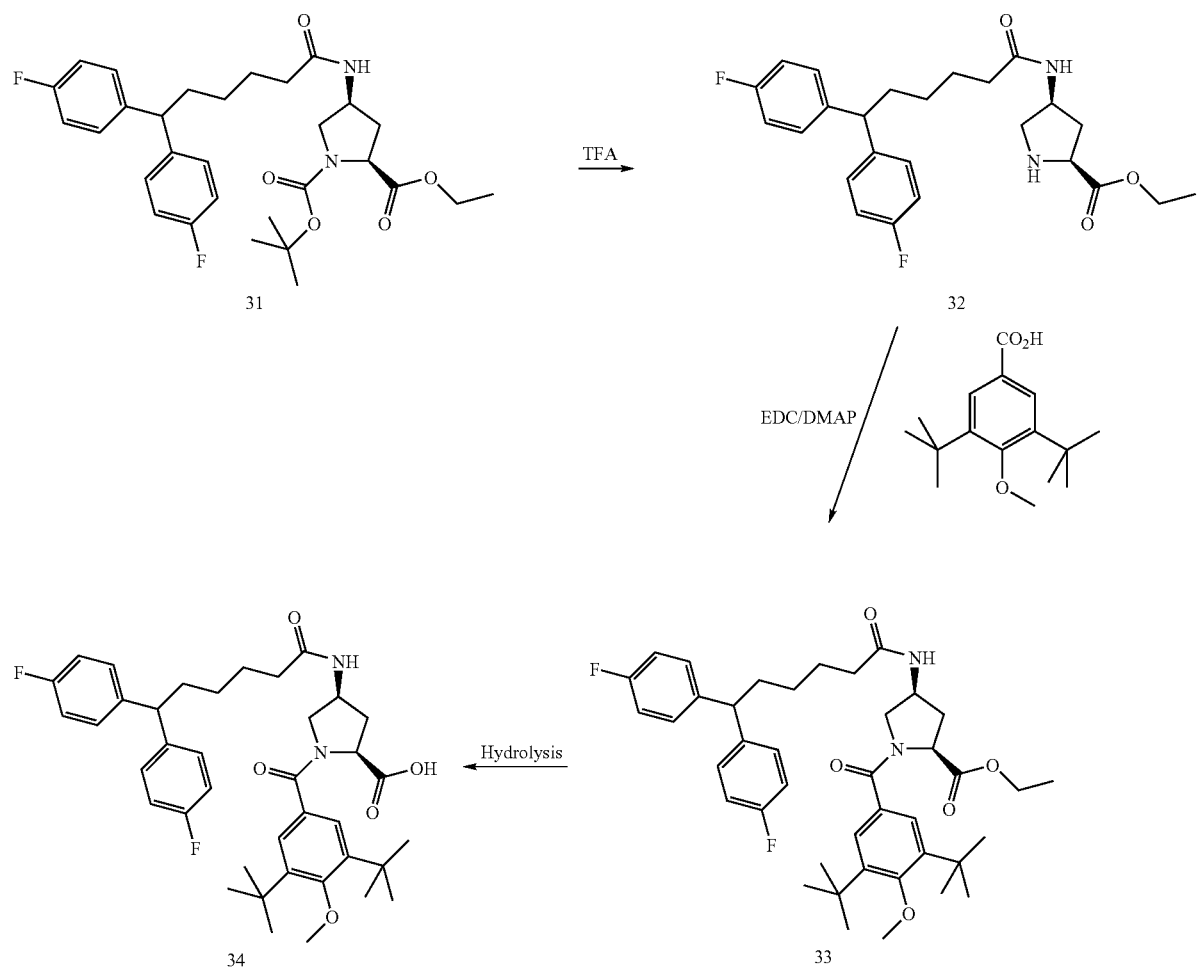
Reaction Scheme G
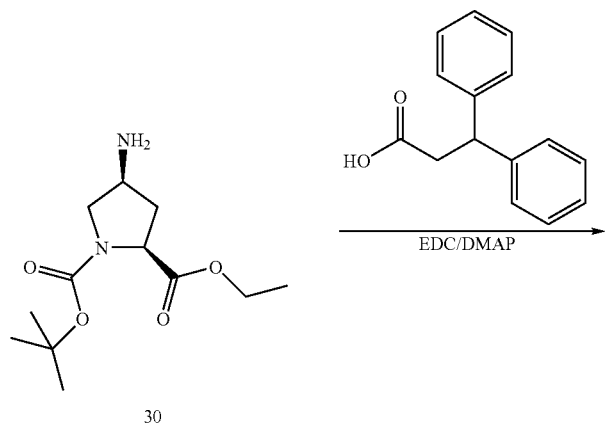

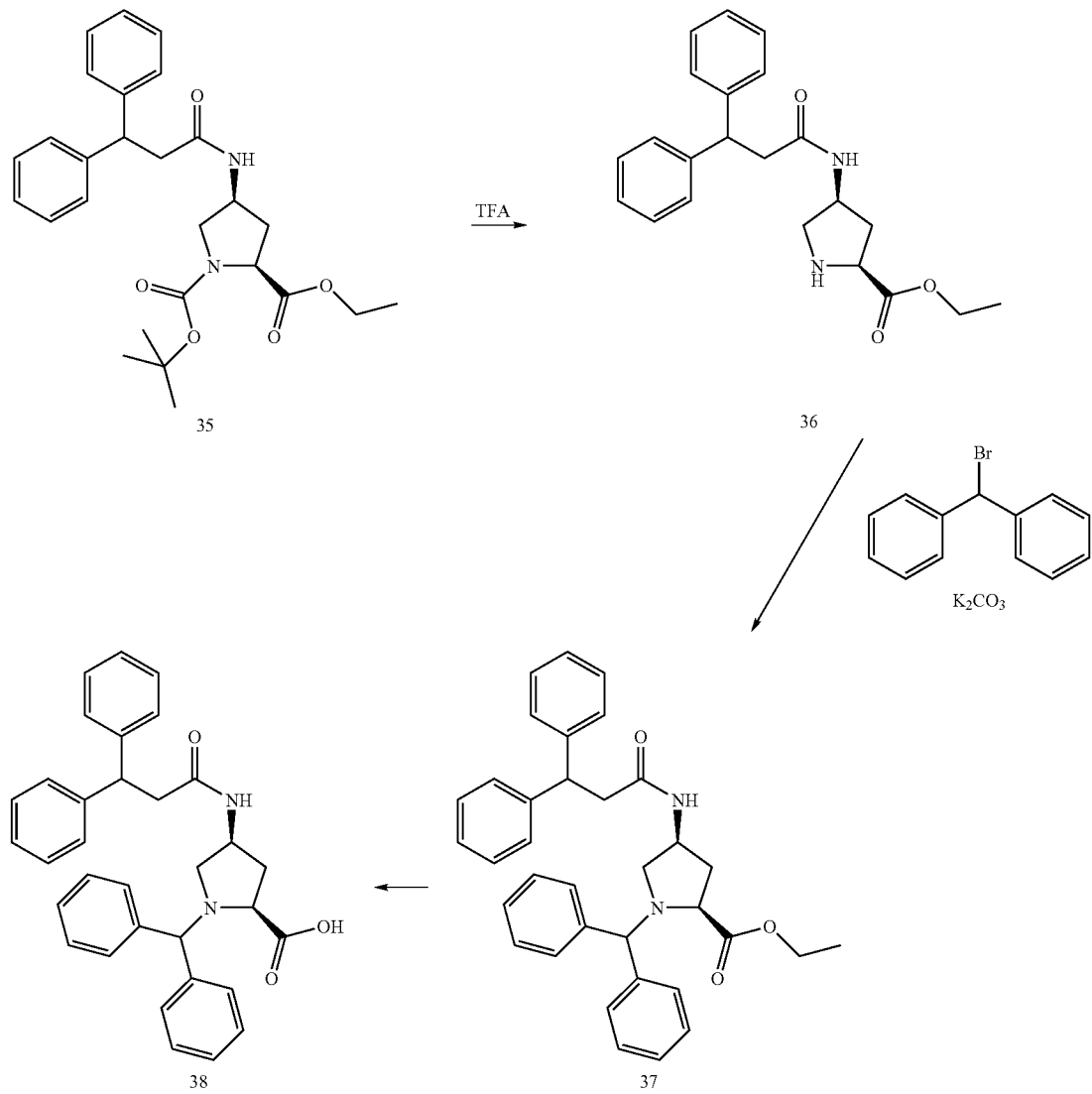
Reaction Scheme H
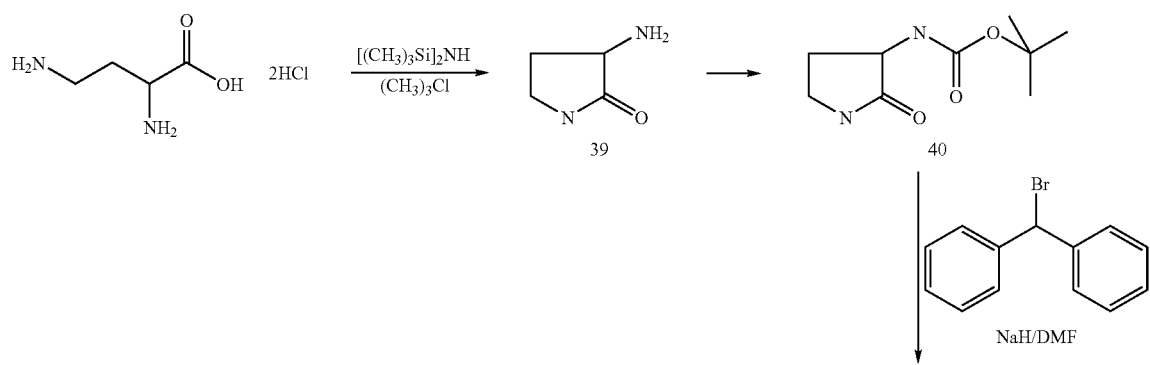

-continued

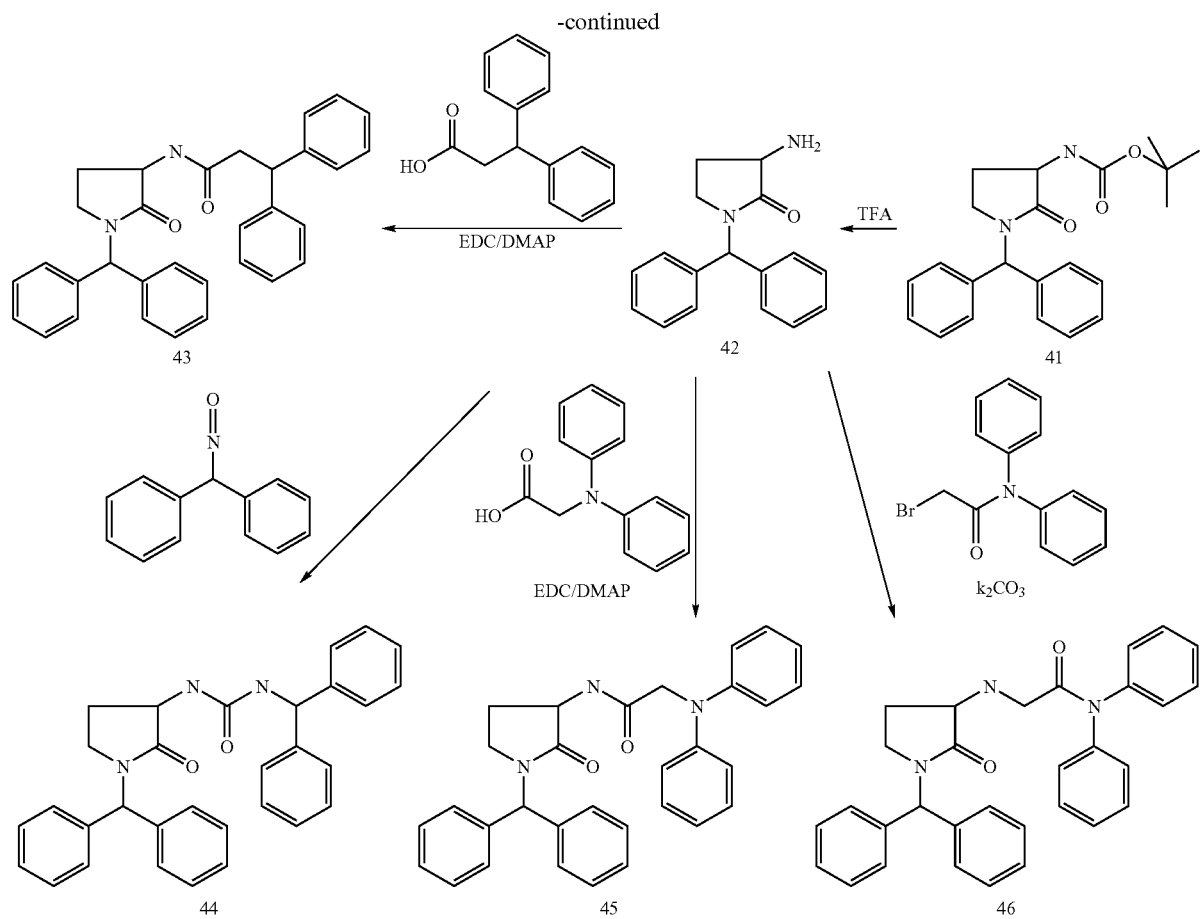

Libraries and Screening

The compounds of the invention can be synthesized individually using methods known in the art, or as members of a combinatorial library. The syntheses of combinatorial libraries are known in the art, and are described for example, in Wentworth, P., Jr., and Janda, K. D., Curr Opin Biotechnol (1998) 9:109-115; Salemme, F. R., et al., Structure (1997) 5:319-324. The libraries contain compounds with various substituents and various degrees of unsaturation, as well as different chain lengths. The libraries may contain as few as 10 members, but typically contain several hundred members to several thousand members. The libraries may then be screened for compounds which are particularly effective against a specific subtype of calcium channel (e.g., the N-type channel).

Methods of performing these screening functions are well known in the art. Typically, the receptor to be targeted is expressed at the surface of a recombinant host cell such as human embryonic kidney cells. Each library compound's ability to bind the channel to be tested is measured, for example, by the ability of the compound to displace a labeled binding ligand. The labeled binding, ligand may be the ligand normally associated with the channel or an antibody to the channel. More typically, the ability to antagonize the receptor is measured in the presence of calcium, barium or other permeant divalent cation and the ability of the compound to interfere with the signal generated is measured using standard techniques.

One method involves the binding of radiolabeled agents that interact with the calcium channel, and subsequent analysis of equilibrium binding measurements including, but not limited to, on rates, off rates, $K_d$ values and competitive binding by other molecules. Another method involves, screening for compound's effect by electrophysiological assay, whereby individual cells are impaled with a microelectrode, and currents through the calcium channel are recorded before and after application of the compound of interest. Another method, high-throughput spectrophotometric assay, utilizes loading of the cell lines with a fluorescent dye sensitive to intracellular calcium concentration, and subsequent examination of the compound's effects, such as the ability of depolarization by potassium chloride or other means to alter intracellular calcium levels.

As described above, a more definitive assay can be used to distinguish inhibitors of calcium flow which operate as open channel blockers, as opposed to those that operate by promoting inactivation of the channel or as resting channel blockers. The methods to distinguish these types of inhibition are described in more particularity in the examples below. In general, open-channel blockers are assessed by measuring the level of peak current when depolarization is imposed on a background resting, potential of about −100 mV in the presence and absence of the candidate compound. Successful open-channel blockers will reduce the peak current observed and may accelerate the decay of this current. Compounds that are inactivated channel blockers are generally determined by their ability to shift the voltage dependence of inactivation towards more negative potentials. This is also reflected in their ability to reduce peak currents at more depolarized holding potentials (e.g., −70 mV) and at higher frequencies of stimulation, e.g., 0.2 Hz vs. 0.067 Hz. Finally, resting channel blockers would diminish the peak current amplitude during the very first depolarization after drug application without additional inhibition during the depolarization.

Utility and Administration

The compounds of the invention can be formulated as pharmaceutical or veterinary compositions for use as treatment of human and animal subjects. Depending on the subject to be treated, the mode of administration, and the type of treatment desired (e.g., prevention, prophylaxis, therapy), the compounds are formulated in ways consonant with these parameters. A summary of such techniques is found in *Remington's Pharmaceutical Sciences,* latest edition, Mack Publishing Co., Easton, Pa., incorporated herein by reference. In general, the compounds of formulas 1 and 2 may be used alone, as mixtures, or in combination with other pharmaceuticals. Depending on the mode of administration, the compounds will be formulated into suitable compositions to permit facile delivery.

Formulations may be prepared in a manner suitable for systemic administration or topical or local administration. Systemic formulations include those designed for injection (e.g., intramuscular, intravenous or subcutaneous injection), or may be prepared for transdermal, transmucosal, or oral administration. The formulation will generally include a diluent as well as, in some cases, adjuvants, buffers, preservatives and the like. The compounds can be administered also in liposomal compositions or as microemulsions.

For injection, formulations can be prepared in conventional forms as liquid solutions or suspensions, or as solid forms suitable for solution or suspension in liquid prior to injection or as emulsions. Suitable excipients include, for example, water, saline, dextrose, glycerol and the like. Such compositions may also contain amounts of nontoxic auxiliary substances such as wetting or emulsifying agents, pH buffering agents and the like, such as, for example, sodium acetate, sorbitan monolaurate, and so forth. Various sustained release systems for drugs have also been devised. See, for example, U.S. Pat. No. 5,624,677.

Systemic administration may also include relatively non-invasive methods such as the use of suppositories, transdermal patches, transmucosal delivery and intranasal administration. Oral administration is also suitable for compounds of the invention. Suitable forms include syrups, capsules, tablets, as understood in the art.

The dosage of the compounds of the invention is typically 0.1-15 mg/kg, preferably 0.1-1 mg/kg for administration to animal or human subjects. However, dosage levels are highly dependent on the nature of the condition, drug efficacy, the condition of the patient, the judgment of the practitioner, and the frequency and mode of administration.

The following preparations and examples are given to enable those skilled in the art to more clearly understand and to practice the present invention. They should not be considered as limiting the scope of the invention, but merely as being illustrative and representative thereof.

EXAMPLE 1

Synthesis of (R)-6,6-Bis-(4-fluoro-phenyl)-hexanoic acid (1-benzyl-pyrrolidin-3-yl)-methyl-amide

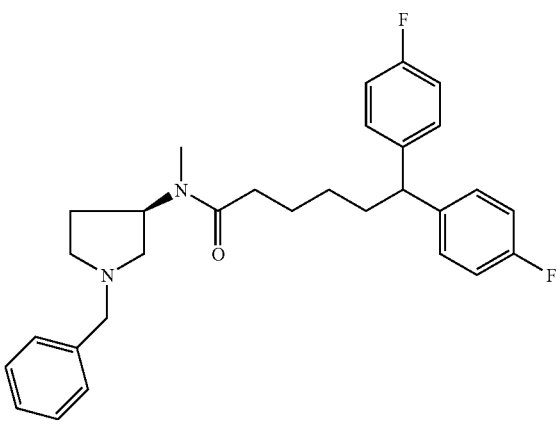

To a solution of(R)-(1-benzyl-pyrrolidin-3-yl)-methyl-amine(0.4 g, 2.1 mmol) in dry $CH_2Cl_2$ (30 ml) was added 6,6-bis-(4-fluorophenyl)-hexanoic acid(0.63 g, 2.1 mmol) under nitrogen. To the reaction was added EDC (0.8 g, 4.2 mmol) and DMAP (cat) and the reaction mixture stirred under nitrogen at room temperature overnight. The reaction was then concentrated under reduced pressure. The residue dissolved in ethyl acetate: water (10:1) (150 ml). The organic was washed with water (30 ml, 2×) and 10% NaOH (30 ml) and dried over $MgSO_4$ and evaporated to dryness. The resulting residue was purified by column chromatography using $CH_2Cl_2:CH_3OH$ (15:1) to give 0.9 g of desired product.

EXAMPLE 2

Synthesis of (R)-6,6-Bis-(4-fluoro-phenyl)-hexanoic acid[1-(3,5-di-tert-butyl-4-methoxy-benzoyl)-pyrrolidin-3-yl]-methyl-amide

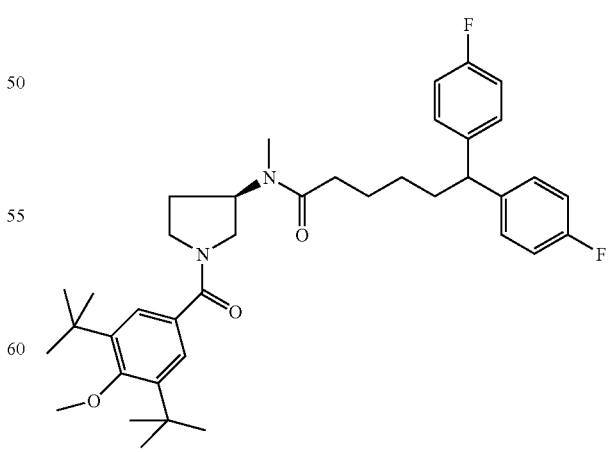

33

A. Synthesis of (R)-6,6-Bis-(4-fluoro-phenyl)-hexanoic acid methyl-pyrrolidin-3-yl-amide

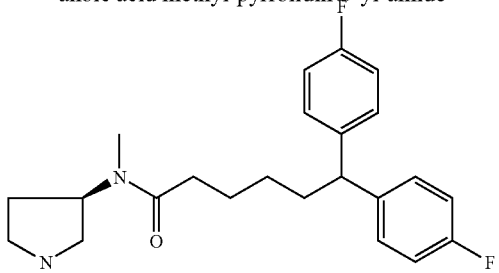

To a solution of 6,6-Bis-(4-fluoro-phenyl)-hexanoic acid (1-benzoyl-pyrrolidin-3-yl)-methyl amide(1.0 g, 2.1 mmol in CH₃OH (50 ml) was added Pd/C 20% (250 mg). The resulting slurry was hydrogenated at 50 psi for 24 hours. The catalyst was filtered through Celite and filtrate evaporated under reduced pressure to give 0.78 g of desired product.

B. Synthesis of Final Product

To a solution of (R)-6,6-Bis-(4-fluoro-phenyl)-hexanoic acid methyl-pyrrolidin-3-yl-amide (0.78 g, 2.02 mmol) in dry CH₂Cl₂ (30 ml) was added 3,5-di-tert-butyl-4-methoxy benzoic acid (0.53 g, 2.02 mmol) under nitrogen. To the reaction was added EDC (0.77 g, 4.04 mmol) and DMAP (cat) and the reaction mixture stirred under nitrogen at room temperature overnight. The reaction was then concentrated under reduced pressure. The residue was dissolved in ethyl acetate: water (10:1) (150 ml). The organic was washed with water (30 ml, 2×) and 10% NaOH (30 ml) and dried over MgSO₄ and evaporated to dryness. The resulting residue was purified by column chromatography using CH₂Cl₂:CH₃OH (15:1) to give 1.1 g of desired product.

EXAMPLE 3

(R)-N-(1-Benzhydryl-pyrrolidin-3-yl)-N-methyl-3,3-diphenyl-propionamide

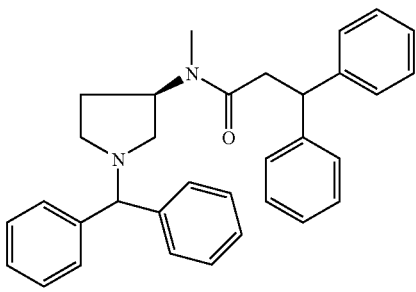

To a solution of bromodiphenylmethane(0.29 g, 1.18 mmol) in butanone (10 ml) was added N-methyl-3,3-diphenyl-N-pyrrolidi-3-yl-propionamide(0.55 g, 1.78 mmol), K₂CO₃ (0.16 g, 1.18 mmol) and KI (0.19 g, 1.18 mmol). The mixture was heated under reflux for 18 hours, then filtered and the solvent was removed in vacuo. The residue was dissolved in CH₂Cl₂ (50 ml) and washed with water (10 ml). Drying over MgSO₄ and removal of solvent under reduced pressure followed by column chromatography using Hex: EtOAc (1:2) gives the desired product.

EXAMPLE 4

Synthesis of (R)-N-Methyl-3,3-diphenyl-N-(1-pyridin-4-ylmethyl-pyrrolidin-3-yl)-propionamide

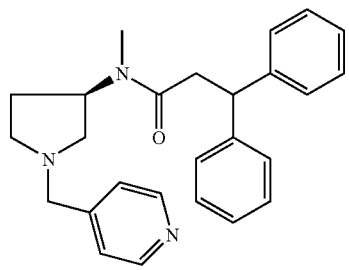

To a solution of N-methyl-3,3-diphenyl-N-pyrrolidin-3-yl-propionamide(0.45 g, 1.46 mmol) in CH₂Cl₂ (10 ml) was added 4-pyridinecarboxaldehyde(0.14 ml, 1.46 mmol), sodium triacetoxyborohydride(0.4 g, 1.89 mmol) and ACOH (0.17 ml, 2.92 mmol). The resulting solution was stirred at room temperature under nitrogen overnight. The reaction mixture was quenched with saturated NaHCO₃ (4 ml), and product was extracted with EtOAc (3×30 ml). Drying the EtOAc extract over MgSO₄ and removal of solvent under reduced pressure followed by column chromatography using acetone:EtOAc (1:1) gives the desired product in good yield.

EXAMPLE 5

Synthesis of (R)-3-Benzhydryl-1-(1-benzyl-pyrrolidin-3-yl)-1-methyl-urea

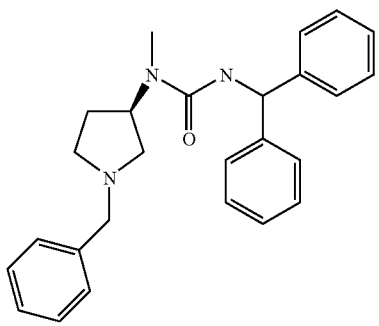

To a solution of (R)-(1-benzoyl-pyrrolidin-3-yl)-methyl-amine(0.32 g, 1.68 mmol) in dry CH₂Cl₂ (5 ml) was added diphenylmethyl isocyanate(0.32 ml, 1.68 mmol) dropwise under nitrogen. The resulting mixture was stirred at room temperature overnight. Removal of solvent under reduced pressure followed by column chromatography using CH₂Cl₂: CH₃OH(15:1) gives 0.65 g of the desired product.

EXAMPLE 6

Synthesis of (R)-3-Benzhydryl-1-(1-benzhydryl-pyrrolidin-3-yl)-1-methyl-urea

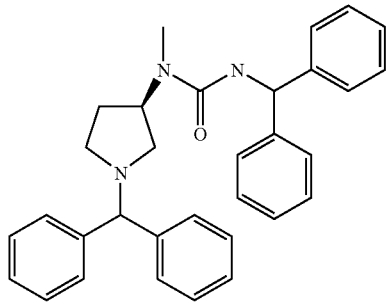

A. Synthesis of (R)-3-Benzhydryl-1-methyl-1-pyrrolidin-3-yl-urea

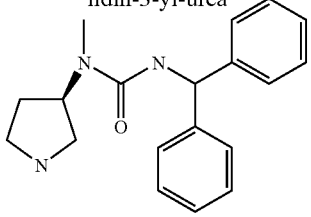

To a solution of 3-benzhydryl-1-(1-benzoyl-pyrrolidin-3-yl)-1-methyl-urea (0.7 g, 1.75 mmol) in CH$_3$OH (25 ml) was added Pd/C 20% (175 mg). The resulting slurry was hydrogenated at 50 psi for 24 hours. The catalyst was filtered through Celite and filtrate evaporated under reduced pressure to, give 0.63 g of desired product.

B. Synthesis of Final Product

To a solution of bromodiphenylmethane (0.43 g, 1.75 mmol) in butanone (10 ml) was added 3-benzhydryl-1-methyl-1-pyrrolidin-3-yl-urea(0.65 g, 2.1 mmol), K$_2$CO$_3$ (0.24, 1.75 mmol) and KI (0.29 g, 1.75 mmol). The mixture was heated under reflux for 18 hours, then filtered and the solvent was removed in vacuo. The residue was dissolved in CH$_2$Cl$_2$ (50 ml) and washed with water (10 ml). Drying over MgSO$_4$ and removal of solvent under reduced pressure followed by column chromatography using Hex:EtOAc (1:1) gives the desired product.

EXAMPLE 7

Synthesis of (R)-N-(1-Benzyl-pyrrolidin-3-yl)-2-diphenylamino-N-methyl-acetamide

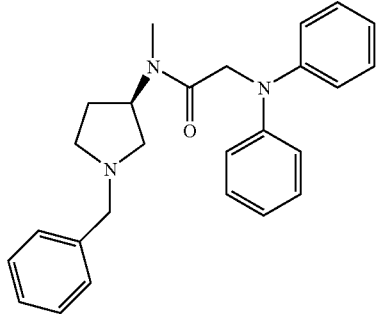

To a solution of (R)-(1-benzoyl-pyrrolidin-3-yl)-methyl-amine(0.32 g, 1.68 mmol) in dry CH$_2$Cl$_2$ (20 ml) was added diphenylaminoacetic acid (0.38 g, 1.68 mmol) under nitrogen. To the reaction was added EDC (0.65 g, 3.36 mmol) and DMAP (cat) and the reaction mixture stirred under nitrogen at room temperature overnight. The reaction was then concentrated under reduced pressure. The residue was dissolved in ethyl acetate: water (10:1) (100 ml). The organic was washed with water (25 ml, 2×) and 10% NaOH (25 ml), dried over MgSO$_4$ and evaporated to dryness. The resulting residue was purified by column chromatography using CH$_2$Cl$_2$:CH$_3$OH (15:1) to give 0.68 g of desired product.

EXAMPLE 8

Synthesis of (R)—N-(1-Benzhydryl-pyrrolidin-3-yl)-2-diphenylamino-N-methyl-acetamide

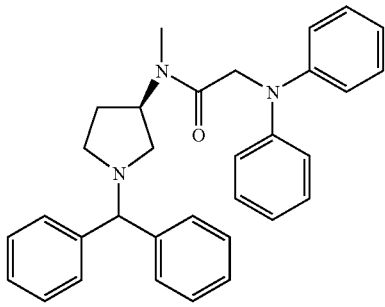

A. Synthesis of (R)-2-Diphenylamino-N-methyl-N-pyrrolidin-3-yl-acetamide

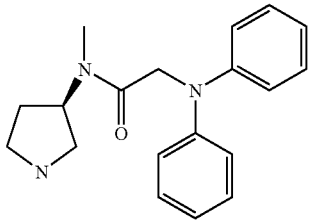

To a solution of (R)—N-(1-benzoyl-pyrrolidin-3-yl)-2-diphenylamino-N-methyl-acetamide (0.68 g, 1.7 mmol) in CH$_3$OH (30 ml) was added Pd/C 20% (170 mg). The resulting slurry was hydrogenated at 50 psi for 24 hours. The catalyst was filtered through Celite and filtrate evaporated under reduced pressure to give 0.6 g of desired product.

B. Synthesis of Final Product

To a solution of bromodiphenylmethane (0.3 g, 1.23 mmol) in butanone (10 ml) was added (R)-2-diphenylamino-N-methyl-N-pyrrolidin-3-yl-acetamide (0.46 g, 1.5 mmol), K$_2$CO$_3$ (0.17 g, 1.23 mmol) and KI (0.2 g, 1.23 mmol). The mixture was heated under reflux for 18 hours, then filtered and the solvent was removed in vacuo. The residue was dissolved in CH$_2$Cl$_2$, (50 ml) and washed with water (10 ml). Drying over MgSO$_4$ and removal of solvent under reduced pressure followed by column chromatography using Hex:EtOAc (3:1) gave the desired product.

EXAMPLE 9

Synthesis of (R)-2-[(1-Benzyl-pyrrolidin-3-yl)methyl-amino]-N,N-diphenyl-acetamide

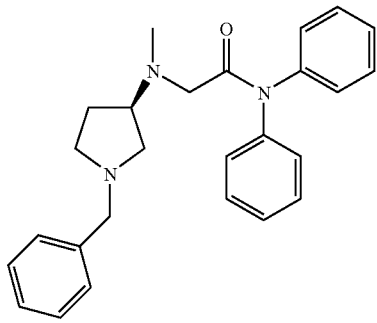

To a solution of (R)-(1-benzoyl-pyrrolidin-3-yl)-methyl-amine(0.32 g, 1.68 mmol) in dry CH₃CN (10 ml) was added 2-bromo-N,N-diphenyl acetamide(0.49 g, 1.68 mmol) and NaHCO₃ (0.28 g, 3.36 mmol) under nitrogen. The reaction mixture was refluxed overnight. After cooling, the solvent was evaporated. The residue was taken up with water (5 ml) and extracted with CHCl₃ (3×25 ml). The organic was dried over MgSO₄ and evaporated to dryness. The resulting residue was purified by column chromatography using CH₂Cl₂:CH₃OH (15:1) to give 680 mg of desired product.

EXAMPLE 10

Synthesis of (R)-2-[(1-Benzhydryl-pyrrolidin-3-yl)-methyl-amino]-N,N-diphenyl-acetamide

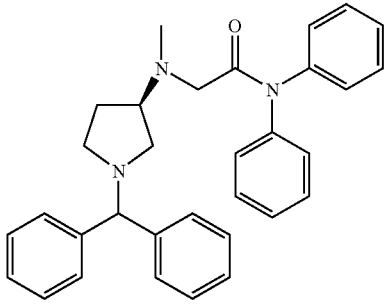

A: Synthesis of (R)-2-(Methyl-pyrrolidin-3-yl-amino)-N,N-diphenyl-acetamide

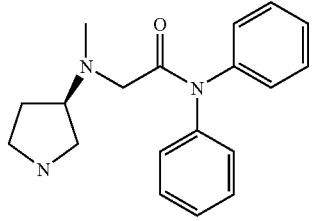

To a solution of (R)-2-[(1-benzoyl-pyrrolidin-3-yl)-methyl-amino]-N,N-diphenyl acetamide(0.68 g, 1.70 mmol) in CH₃OH (30 ml) was added Pd/C 20% (170 mg). The resulting slurry was hydrogenated at 50 psi for 24 hours. The catalyst was filtered through Celite and filtrate evaporated under reduced pressure to give 0.5 g of desired product.

B: Synthesis of Final Product

To a solution of bromodiphenylmethane (0.33 g, 1.34 mmol) in butanone (10 ml) was added (R)-2-(methyl-pyrrolidin-3-yl-amino)-N,N-diphenyl acetamide(0.5 g, 1.61 mmol), K₂CO₃ (0.18 g, 1.34 mmol) and KI (0.22 g, 1.34 mmol). The mixture was heated under reflux for 18 hours, then filtered and the solvent was removed in vacuo. The residue was dissolved in CH₂Cl₂ (50 ml) and washed with water (10 ml). Drying over MgSO₄ and removal of solvent under reduced pressure followed by column chromatography using Hex:EtOAc (1:1) gave the desired product.

EXAMPLE 11

Synthesis of (2S,4S)-4-[6,6-Bis-(4-fluoro-phenyl)-hexanoylamino]-1-(3,5-di-tert-butyl-4-methoxy-benzoyl)-pyrrolidine-2-carboxylic acid ethyl ester

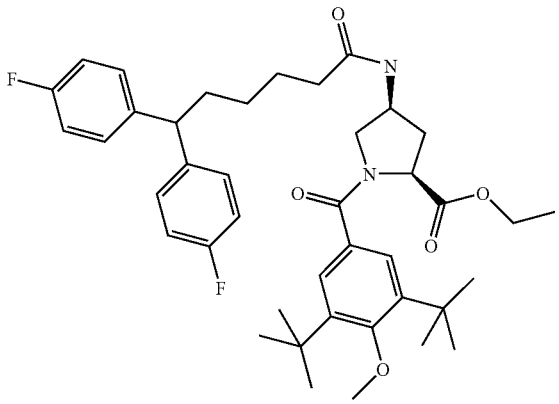

A. Synthesis of (2S,4R)-4-hydroxy-pyrrolidine-1,2-dicarboxylic acid-1-tert-butyl ester-2-ethyl ester

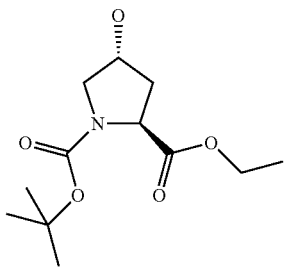

To a solution of (4R)-(tert-Butoxycarbonyl)-4-hydroxy-L-proline (26) (0.92 g, 4.0 mmol) in dry CH₂Cl₂ (30 ml) was added ethanol (1 ml, 21 mmol). To the reaction was added DCC (1.64 g, 8.0 mmol) and DMAP (cat) and the reaction mixture was stirred under nitrogen at room temperature overnight. The reaction was then concentrated under reduced pressure. The residue was dissolved in ethyl acetate: water (10:1) (100 ml). The organic was washed with water (30 ml, 2×) and 10% NaOH (10 ml), dried over MgSO₄ and evaporated to dryness. The resulting residue was purified by column chromatography using CH₂Cl₂:CH₃OH (10:1)to give 1.8 g oil as desired product.

B. Synthesis of (2S,4R)-4-(toluene-4-sulfonyloxy)-pyrrolidine-1,2-dicarboxylic acid-1-tert-butyl ester-2-ethyl ester

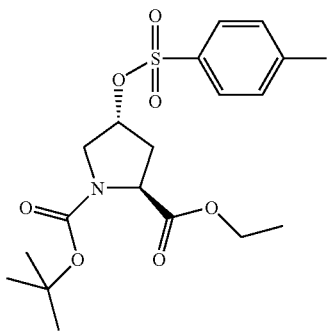

To the solution of (2S,4R)-4-hydroxy-pyrrolidine-1,2-dicarboxylic acid-1-tert-butyl ester-2-ethyl ester (27) (1.8 g, 7 mmol) in dry pyridine (40 ml) was added p-toluenesulfonyl chloride (4.0 g, 21 mmol) under nitrogen at 0° C. The reaction mixture was kept refrigerated at 0° C. for 2 days. The reaction was then concentrated under reduced pressure. The residue was dissolved in ethyl acetate: water (10:1) (150 ml). The organic was washed with water (30 ml, 2×), dried over $MgSO_4$ and evaporated to dryness. The resulting residue was purified by column chromatography using pet ether: EtOAc (1:1) to give 2.6 g of desired product.

C. Synthesis of (2S,4S)-4-azido-pyrrolidin-1,2-dicarboxylic acid-1-tert-butyl ester-2-ethyl ester

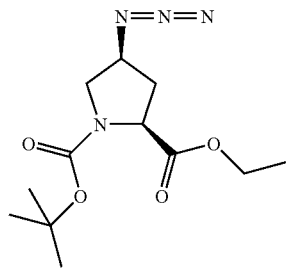

To the solution of (2S,4R)-4-(toluene-4-sulfonyloxy)-pyrrolidine-1,2-dicarboxylic acid-1-tert-butyl ester-2-ethyl ester) (28) (2.6 g, 6.3 mmol) in dry DMF (15 ml) was added $NaN_3$ (0.41 g, 6.3 mmol). The reaction mixture was stirred at room temperature overnight. The reaction mixture was then concentrated under reduced pressure. The residue was dissolved in ethyl acetate: water (10:1) (150 ml). The organic layer was washed with water (30 ml, 2×), dried over $MgSO_4$ and evaporated to dryness The resulting residue was purified by column chromatography using pet ether: $CH_2Cl_2$: MeOH (10:1) to give 1.8 g of desired product.

D. Synthesis of (2S,4S)-4-amino-pyrrolidine-1,2-dicarboxylic acid-1-tert-butyl ester-2-ethyl ester

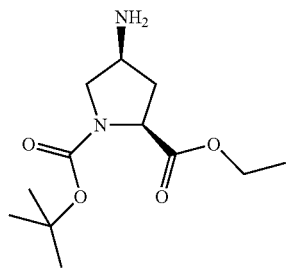

To the solution of (2S,4S)-4-azido-pyrrolidin-1,2-dicarboxylic acid-1-tert-butyl ester-2-ethyl ester (29) (1.8 g, 2.1 mmol) in $CH_3OH$ (40 ml) was added Pd/C 10% (50 mg). The resulting slurry was hydrogenated at 1 atm for 24 hours. The catalyst was filtered through Celite and filtrate evaporated under reduced pressure to give 0.95 g of desired product.

E. Synthesis of (2S,4S)-[6,6-bis-(4-fluoro-phenyl)-hexanoylamino]pyrrolidine-1,2-dicarboxylic acid-1-tert-butyl ester-2-ethyl ester

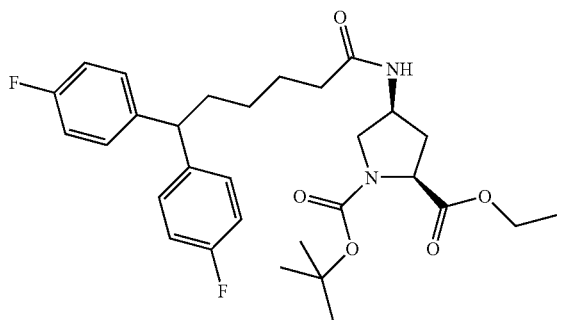

To the solution of (2S,4S)-4-amino-pyrrolidine-1,2-dicarboxylic acid-1-tert-butyl ester-2-ethyl ester (30) (0.5 g, 2 mmol in dry $CH_2Cl_2$ (30 ml) was added 6,6-bis-(4-fluorophenyl)-hexanoic acid (0.62 g, 2 mmol). To the reaction was added EDC (0.77 g, 4 mmol) and DMAP (cat) and the reaction mixture was stirred under nitrogen at room temperature overnight. The reaction was then concentrated under reduced pressure. The residue was dissolved in ethyl acetate: water (10:1)(150 ml). The organic was washed with water (30 ml, 2×) and 10% NaOH (10 ml), dried over $MgSO_4$ and evaporated to dryness. The resulting residue was purified by column chromatography using pet ether: EtOAc (1:1) to give 0.6 g of desired product.

F. Synthesis of (2S,4S)-4-[6,6-bis-(4-fluoro-phenyl)-hexanoylamino]-pyrrolidine-2-carboxylic acid ethyl ester

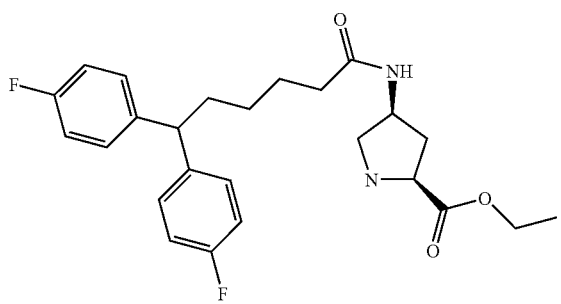

To the solution of (2S,4S)-4-amino-pyrrolidine-1,2-dicarboxylic acid-1-tert-butyl ester-2-ethyl ester (31) (0.6 g, 1.1 mmol) in $CH_2Cl_2$ (20 ml) was added $CF_3CO_2H$ (8 ml). The resulting mixture was stirred under nitrogen for three hours. The reaction was then concentrated under reduced pressure. The residue was neutralized with saturated sodium bicarbonate and extracted twice with ethyl acetate. The organic layer was dried over $MgSO_4$ and evaporated to dryness. The resulting residue was used for next reaction without purification.

G. Synthesis of Final Product

To the solution of (2S,4S)-4-[6,6-Bis-(4-fluoro-phenyl)-hexanoylamino]-pyrrolidine-2-carboxylic acid ethyl ester (32) (0.39 g, 0.88 mmol) in dry $CH_2Cl_2$ (20 ml) was added 3,5-di-tert-butyl-4-methoxy benzoic acid (0.23 g, 0.88 mmol). To the reaction was added EDC (0.34 g, 1.76 mmol)

and DMAP (cat), and the reaction mixture stirred under nitrogen at room temperature overnight. The reaction was then concentrated under reduced pressure. The residue was dissolved in ethyl acetate: water (10:1) (150 ml). The organic was washed with water (30 ml, 2×) and 10% NaOH (10 ml), dried over MgSO$_4$ and evaporated to dryness. The resulting residue was purified by column chromatography using pet ether: EtOAc (1:1) to give 0.46 g of desired product.

EXAMPLE 12

Synthesis of (2S,4S)-4-[6,6-Bis-(4-fluoro-phenyl)-hexanoylamino]-1-(3,5-di-tert-butyl-4-methoxy-benzoyl)-pyrrolidine-2-carboxylic acid

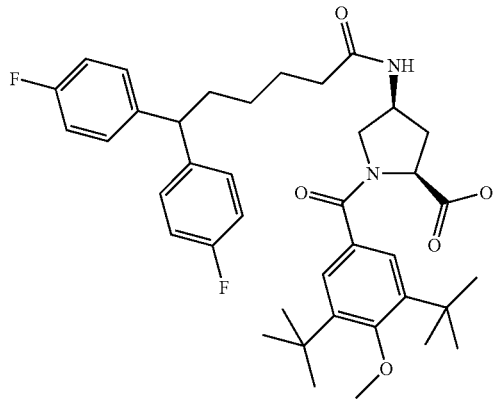

To the solution of (2S,4S)-4-[6,6-Bis-(4-fluoro-phenyl)-hexanoylamino]-1-(3,5-di-tert-butyl-4-methoxy-benzoyl)-pyrrolidine-2-carboxylic acid ethyl ester (33) (0.32 g, 0.52 mmol) in THF (15 ml), MeOH (5 ml) and water (5 ml) was added LiOH (0.1 g, 2.45 mmol), and the reaction mixture was stirred at room temperature overnight. The reaction was then concentrated under reduced pressure. The residue was neutralized with 2N HCl to pH~2 and dissolved in ethyl acetate: water (10:1) (150 ml). The organic was washed with water (30 ml, 2×), dried over MgSO$_4$ and evaporated to dryness. The resulting residue was purified by column chromatography using CH$_2$Cl$_2$: MeOH (10:1) to give 0.26 g of desired product.

EXAMPLE 13

Synthesis of (2S,4S)-1-benzhydryl-4-(3,3-diphenyl-propionylamino)-pyrrolidine-2-carboxylic acid ethyl ester

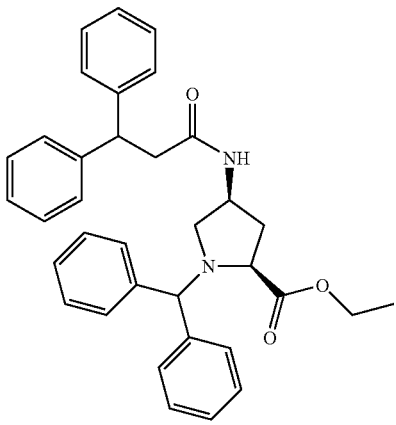

A. Synthesis of (2S,4S)-4-(3,3-diphenylamino)-pyrrolidine-1,2-dicarboxylic acid-1-tert-butyl ester-2-ethyl ester

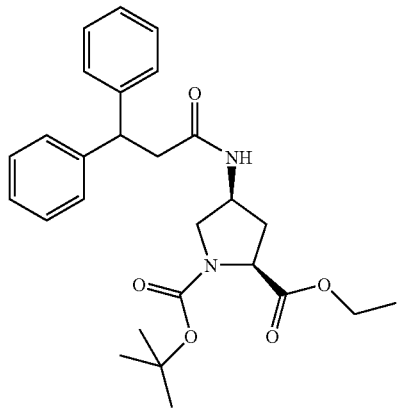

To a solution of (2S,4S)-4-amino-pyrrolidine-1,2-dicarboxylic acid-1-tert-butyl ester-2-ethyl ester (30)(0.512 g, 2 mmol) in dry CH$_2$Cl$_2$ (20 ml) was added 3,3-diphenyl-propanoic acid (0.452 g, 2 mmol). To the reaction was added EDC (0.76 g, 4 mmol) and DMAP (cat), and the reaction mixture was stirred under nitrogen at room temperature overnight. The reaction was then concentrated under reduced pressure. The residue as dissolved in ethyl acetate: water (10:1) (150 ml). The organic was washed with water (30 ml, 2×) and 10% NaOH (10 ml), dried over MgSO$_4$ and evaporated to dryness. The resulting residue was purified by column chromatography using CH$_2$Cl$_2$:CH$_3$OH (15:1) to give 0.78 g of desired product.

B. Synthesis of (2S,4S)-4-(3,3-diphenyl-propionylamino)-pyrrolidine-2-carboxylic acid ethyl ester

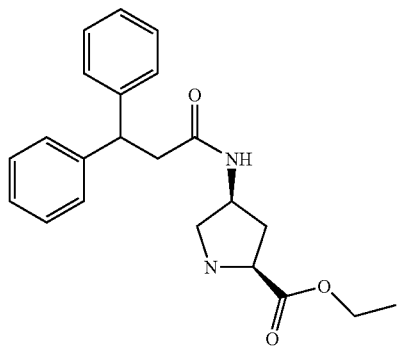

To the solution of (2S,4S)-4-(3,3-diphenylamino)-pyrrolidine-1,2-dicarboxylic acid-1-tert-butyl ester-2-ethyl ester (35) (0.78 g, 1.7 mmol) in CH$_2$Cl$_2$ (20 ml) was added CF$_3$CO$_2$H (8 ml). The resulting mixture was stirred under nitrogen at room temperature for 3 hours. The reaction was then concentrated under reduced pressure. The residue was neutralized with sodium carbonate and extracted twice with ethyl acetate: water (10:1) (150 ml). The organic was washed with water (30 ml, 2×) and 10% NaOH (10 ml), dried over MgSO$_4$ and evaporated to dryness. The resulting residue was used for next reaction without any further purification.

C. Synthesis of Final Product

To a solution of bromodiphenylmethane (0.4 g, 1.64 mmol) in butanone (10 ml) was added (2S,4S)-4-(3,3-diphenyl-propionylamino)-pyrrolidine-2-carboxylic acid ethyl ester (36) (0.6 g, 1.64 mmol), K$_2$CO$_3$ (0.23 g, 1.64 mmol) and KI (0.27 g, 1.64 mmol). The mixture was heated under reflux for 18 hours, and then filtered and the solvent was removed in vacuo. The residue was dissolved in CH$_2$Cl$_2$ (50 ml) and washed with water (10 ml). Drying over MgSO$_4$ and removal of solvent under reduced pressure followed by column chromatography using Hex:EtOAc (1:1) gives 0.5 g the desired product.

EXAMPLE 14

Synthesis of (2S,4S)-1-benzhydryl-4-(3,3-diphenyl-propionylamino)-pyrrolidine-2-carboxylic acid

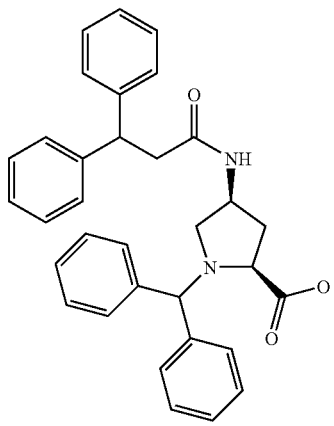

To the solution of (2S,4S)-1-benzhydryl-4-(3,3-diphenyl-propionylamino)-pyrrolidine-2-carboxylic acid ethyl ester (37) (0.25 g, 0.5 mmol) in THF (15 ml), MeOH (5 ml) and water (5 ml) was added LiOH (0.1 g, 2.45 mmol), and the reaction mixture was stirred at room temperature overnight. The reaction was then concentrated under reduced pressure. The residue was neutralized with 2N HCl to pH~2 and dissolved in ethyl acetate: water (10:1) (150 ml). The organic was washed with water (30 ml, 2×), dried over MgSO$_4$ and evaporated to dryness. The resulting residue was purified by column chromatography using CH$_2$Cl$_2$: MeOH (10:1) to give 0.12 g of desired product.

EXAMPLE 15

Synthesis of N-(1-Benzhydryl-2-oxo-pyrrolidin-3-yl)-3,3-diphenyl-propionamide

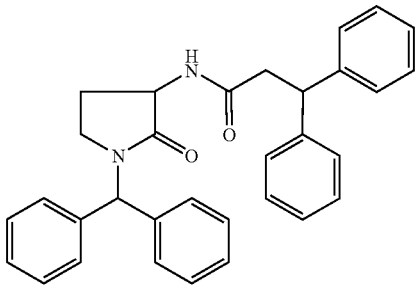

A. Synthesis of 3-amino-pyrrolidin-2-one

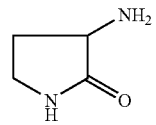

Diaminobutyric acid (5 g, 26.16 mmol), xylene (450 ml), hexamethyldisilazane (40 ml, 183.12 mmol) and a few drops of chlorotrimethylsilane was heated under reflux and gentle stream of nitrogen for 48 hours (complete solution occurs after 3-5 hours), then cooled and poured into absolute ethanol (100 ml), and evaporated under vacuum to dryness. The residue was filtered and washed with ether to give a desired product in 98% yield.

B. Synthesis of (2-oxo-pyrrolidin-3-yl)-carbamic acid tert-butyl ester

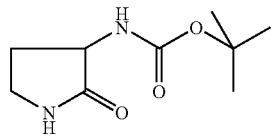

To a solution of 3-amino-pyrrolidin-2-one (39) (2.8 g, 28 mmol) in [methanol:triethylamine (9:1)] (130 ml), was added di-tert-butyldicarbonate (6.7 g, 30.8 mmol). The mixture was stirred overnight followed by refluxing for two hours. Solvent was removed and solid was filtered and washed with ether to give the desired product in 97% yield.

C. Synthesis of (1-Benzhydryl-2-oxo-pyrrollidin-3-yl)-carbamic acid tert-butyl ester

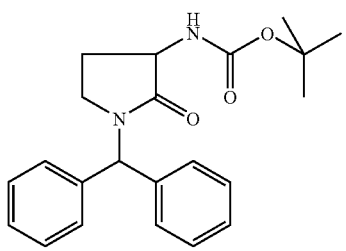

To a solution of(2-oxo-pyrrolidin-3-yl)-carbamic acid tert-butyl ester (40) (1 g, 5 mmol) in dry DMF (25 ml) was added sodium hydride (60%, 240 mg, 6 mmol) followed by addition of bromodiphenylmethane (1.36 g, 5.5 mmol). The mixture was heated at 100° C. for 18 hours, then cooled and the solvent was removed in vacuo. The residue was dissolved in ethyl acetate (50 ml) and washed with water (2×10 ml). Drying over MgSO$_4$ and removal of solvent under reduced pressure gave a solid that was then washed with ether to give the desired product in 93% yield.

D. Synthesis of 3-Amino-1-benzhydryl-pyrrolidin-2-one

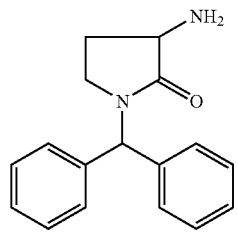

To the solution of (1-benzhydryl-2-oxo-pyrrollidin-3-yl)-carbamic acid tert-butyl ester (41) (1.2 g, 3.26 mmol) in $CH_2Cl_2$ (20 ml) was added $CF_3CO_2H$ (8 ml). The resulting mixture was stirred under nitrogen at room temperature overnight. The reaction was then concentrated under reduced pressure. The residue was dissolved in ethyl acetate and washed with saturated sodium hydrogen carbonate (20 ml). The organic was dried over $MgSO_4$ and evaporated to dryness. The resulting residue was purified by column chromatography using $CH_2Cl_2$: MeOH (10:1) to give the desired product in 97% yield.

E. Synthesis of Final Product

To a solution of 3-amino-1-benzhydryl-pyrrolidin-2-one (42) (0.2 g, 0.75 mmol) in dry $CH_2Cl_2$ (20 ml)was added 3,3-diphenylpropionic acid (0.19 g, 0.82 mmol) under nitrogen. To the reaction was added EDC (0.18 g, 0.9 mmol) and DMAP (cat), and the reaction mixture was stirred under nitrogen at room temperature overnight. The reaction was then concentrated under reduced pressure. The residue was dissolved in ethyl acetate: water (10:1) (100 ml). The organic was washed with water (25 ml, 2×) and 10% NaOH (25 ml), dried over $MgSO_4$ and evaporated to dryness. The resulting residue was purified by column chromatography using hexane:ethyl acetate (2:1) to give the desired product in 70% yield

EXAMPLE 16

Synthesis of 1-Benzhydryl-3-(1-benzhydryl-2-oxo-pyrrolidin-3-yl)-urea

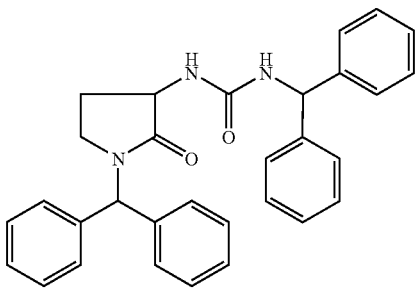

To a solution of 3-amino-1-benzhydryl-pyrrolidin-2-one (42) (0.2 g, 0.75 mmol) in dry $CH_2Cl_2$ (15 ml) was added diphenylmethyl isocyanate (0.17 mg, 0.82 mmol) dropwise under nitrogen. The resulting mixture was stirred at room temperature for two days followed by refluxing for 5 hours. Removal of solvent under reduced pressure followed by column chromatography using hexane: ethyl acetate (2:1) gave the desired product in 65% yield.

EXAMPLE 17

Synthesis of N-(1-Benzhydryl-2-oxo-pyrrolidin-3-yl)-2-diphenylamino-acetamide

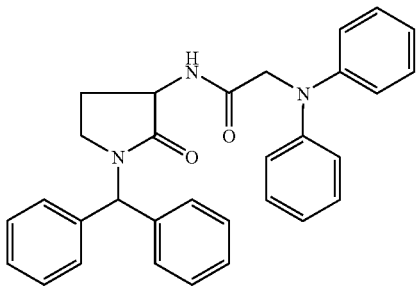

To a solution of 3-amino-1-benzhydryl-pyrrolidin-2-one (42) (0.2 g, 0.75 mmol) in dry $CH_2Cl_2$ (20 ml)was added diphenylamino ethanoic acid (0.19 g, 0.82 mmol) under nitrogen. To the reaction was added EDC (0.18 g, 0.9 mmol) and DMAP (cat) and the reaction mixture was stirred under nitrogen at room temperature overnight. The reaction was then concentrated under reduced pressure. The residue was dissolved in ethyl acetate:water (10:1) (100 ml). The organic was washed with water (25 ml, 2×) and 10% NaOH (25 ml), dried over $MgSO_4$ and evaporated to dryness. The resulting residue was purified by column chromatography using hexane:ethyl acetate (2:1) to give the desired product in 69% yield.

EXAMPLE 18

Synthesis of 2-(1-Benzhydryl-2-oxo-pyrrolodin-3-yl-amino)-N,N-diphenyl acetamide

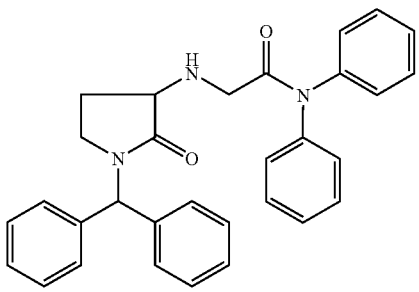

To a solution of 3-amino-1-benzhydryl-pyrrolidin-2-one (42) (0.2 g, 0.75 mmol in dry DMF (15 ml) was added 2-bromo-N,N-diphenyl acetamide (0.24 g, 0.82 mmol) and NaH (50 mg) under nitrogen. The reaction mixture was heated at 100 degrees overnight. After cooling, the solvent was evaporated and residue was taken up with ethyl acetate (50 ml) and washed with water (2×10 ml). The organic was dried over $MgSO_4$ and evaporated to dryness. The resulting residue was purified by column chromatography using hexane:ethyl acetate (2:1) to give desired product in 73% yield.

EXAMPLE 19

Assessment of Calcium Channel Blocking Activity

Calcium channel blocking activity was measured using whole cell patch recordings on human embryonic kidney cells transiently expressing rat $\alpha_{1B}+\alpha_2\delta+\beta_{1b}$ channels (N-type channels) with 5 mM barium as a charge carrier. Channel block was also measured in P/Q-type channels ($\alpha_{1A}+\alpha_2\delta+\beta_{1b}$ cDNA subunits) and L-type channels ($\alpha_{1C}+\alpha_2\delta+\beta_{1b}$ cDNA subunits).

HEK 293 Host cells (ATCC# CRL 1573) were grown in standard DMEM medium supplemented with 2 mM glutamine and 10% fetal bovine serum. HEK 293 cells were transfected by a standard calcium-phosphate-DNA coprecipitation method using the rat $\alpha_{1B}+\beta_{1b}+\alpha_2\delta$ N-type calcium channel subunits in a vertebrate expression vector (for example, see Current Protocols in Molecular Biology).

After an incubation period of 24 to 72 hours, the culture medium was removed and replaced with external recording solution (see below). Whole cell patch clamp experiments were performed using an Axopatch 200B amplifier (Axon Instruments, Burlingame, Calif.) linked to an IBM compatible personal computer equipped with pCLAMP software. Borosilicate glass patch pipettes (Sutter Instrument Co., Novato, Calif.) were polished (Microforge, Narishige, Japan) to a resistance of about 4 MΩ when filled with cesium methanesulfonate internal solution (composition in MM: 109 CsCH$_3$ SO$_4$, 4 MgCl$_2$, 9 EGTA, 9 HEPES, pH 7.2). Cells were bathed in 5 mM Ba$^{++}$ (in mM: 5 BaCl$_2$, 1 MgCl$_2$, 10 HEPES, 40 tetraethylammonium chloride, 10 glucose, 87.5 CsCl pH 7.2). Current data shown were elicited by a train of 100 ms test pulses at 0.066 Hz from −100 mV and/or −80 mV to various potentials (min. −20 mV, max. +30 mV). Drugs were perfused directly into the vicinity of the cells, using a microperfusion system.

Normalized dose-response curves were fit (Sigmaplot 4.0, SPSS Inc., Chicago, Ill.) by the Hill equation to determine IC$_{50}$ values. Steady-state inactivation curves were plotted as the normalized test pulse amplitude following 5 s inactivating prepulses at +10 mV increments. Inactivation curves were fit (Sigmaplot 4.0) with the Boltzman equation, $I_{peak}$ (normalized)=$1/(1+\exp((V-V_h)z/25.6))$, where V and V$_h$ are the conditioning and half inactivation potentials, respectively, and z is the slope factor.

The same protocol was followed for cell lines expressing P/Q-type channels and L-type channels.

FIG. 2 is a graph that shows the selectivity of compound P1 for N-type calcium channels over L-type and P/Q-type channels. P1 is approximately 23-fold more selective for N-type over P/Q-type channels and 75-fold more selective for N-type over L-type channels.

Figure 3:
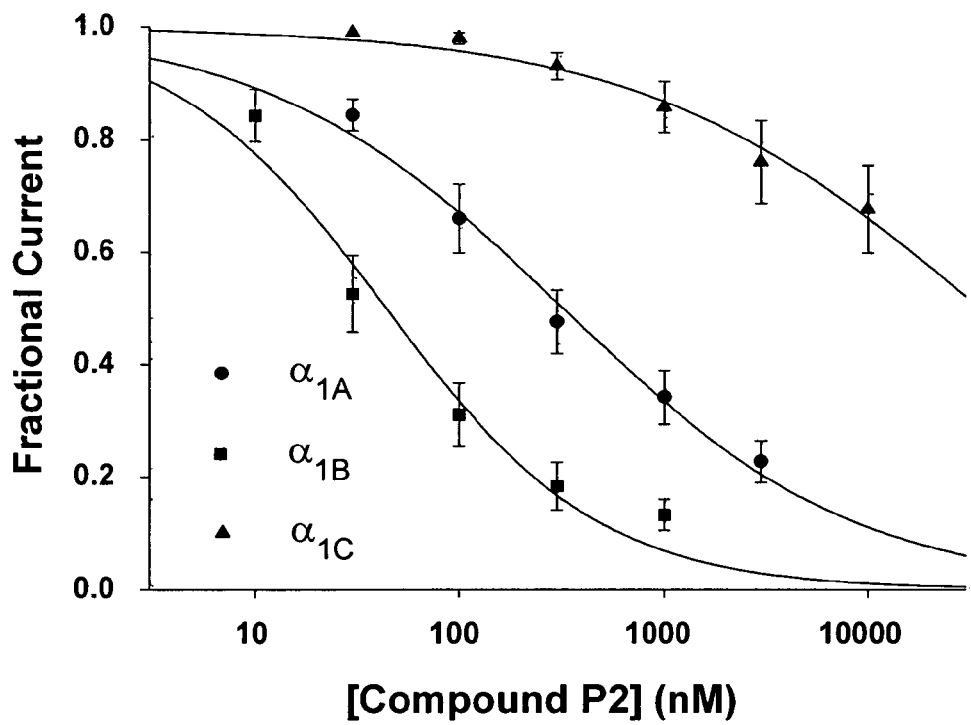
FIG. 3 is a graph showing the selectivity of compound P2 for N—, P/Q- and L-type channels.

FIG. 3 is a graph that shows the selectivity of compound P2 for N-type calcium channels over L-type and P/Q-type channels. P2 is approximately 9-fold more selective for N-type over P/Q-type channels and greater than 1000-fold selective for N-type over L-type channels.

Figure 4:
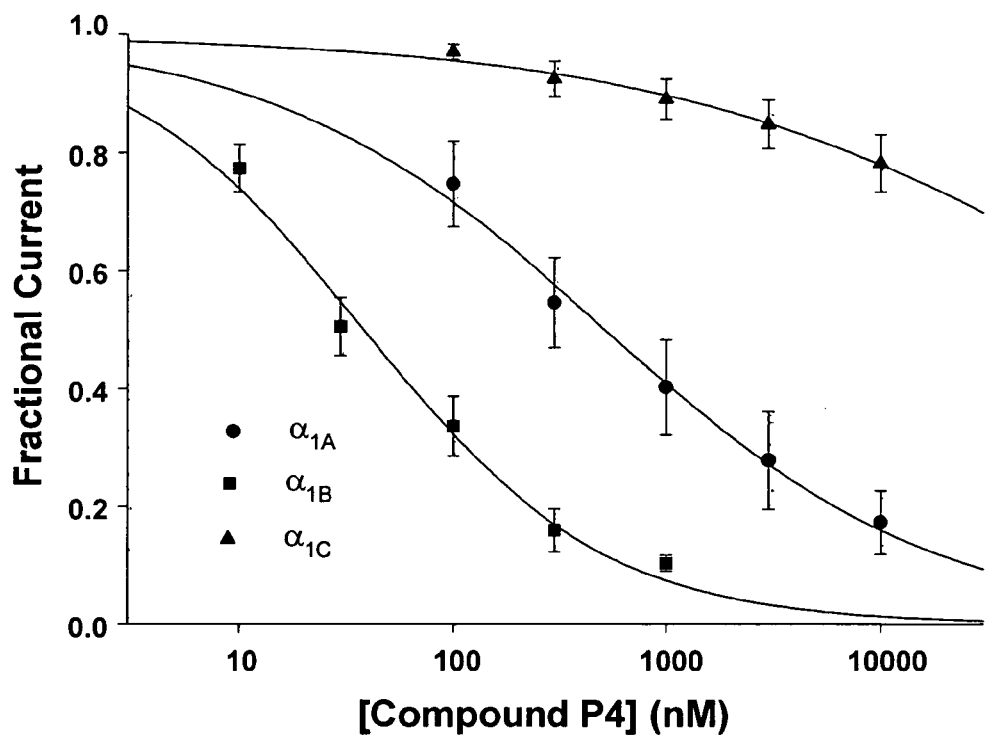
FIG. 4 is a graph showing the selectivity of compound P4 for N—, P/Q- and L-type channels.

FIG. 4 is a graph that shows the selectivity of compound P4 for N-type calcium channels over L-type and P/Q-type channels. P4 is approximately 12-fold more selective for N-type over P/Q-type channels and greater than 5000-fold selective for N-type over L-type channels.

Figure 5:
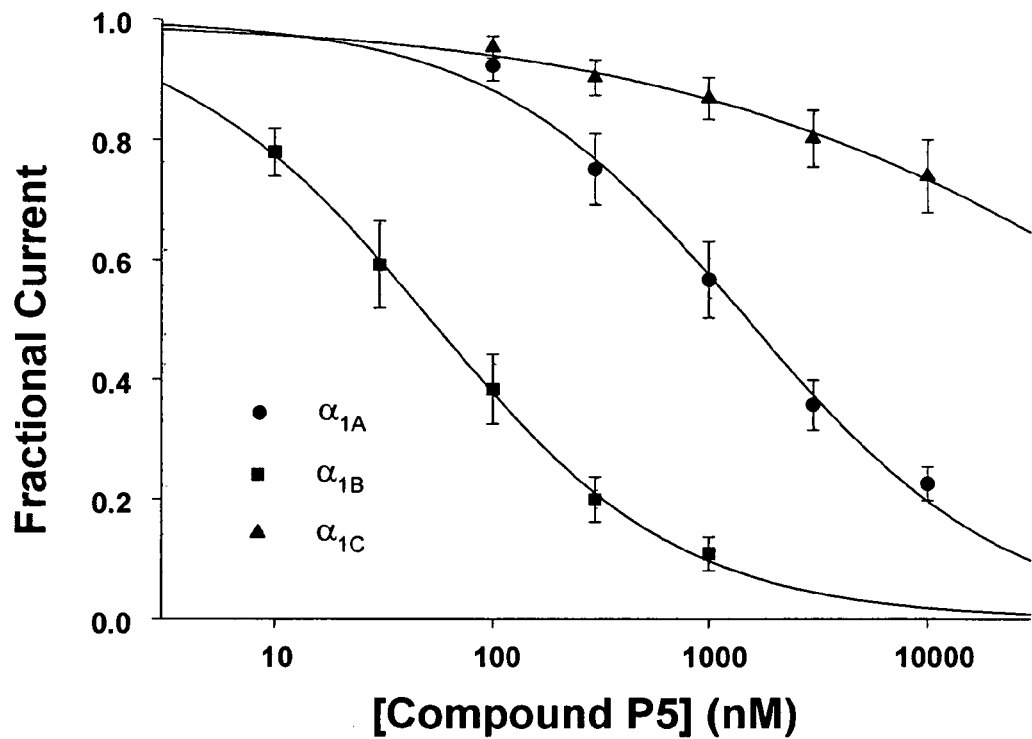
FIG. 5 is a graph showing the selectivity of compound P5 for N—, P/Q- and L-type channels.

FIG. 5 is a graph that shows the selectivity of compound P2 for N-type calcium channels over L-type and P/Q-type channels. P5 is approximately 31-fold more selective for N-type over P/Q-type channels and greater than 2000-fold selective for N-type over L-type channels.

EXAMPLE 20

N-type Channel Blocking Activities of Various Invention Compounds

The methods of Example 11 were followed with slight modifications as will be apparent from the description below.

A. Transformation of HEK Cells

N-type calcium channel blocking activity was assayed in human embryonic kidney cells, HEK 293, stably transfected with the rat brain N-type calcium channel subunits ($\alpha_{1B}+\alpha_2\delta+\beta_{1b}$ cDNA subunits). Briefly, cells were cultured in Dulbecco's modified eagle medium (DMEM) supplemented with 10% fetal bovine serum, 200 U/ml penicillin and 0.2 mg/ml streptomycin at 37° C. with 5% CO$_2$. At 85% confluency, cells were split with 0.25% trypsin/1 mM EDTA and plated at 10% confluency on glass coverslips. At 12 hours the medium was. replaced and the cells transfected using a standard calcium phosphate protocol and the appropriate calcium channel cDNAs. Fresh DMEM was supplied and the cells transferred to 28° C./5% CO$_2$. Cells were incubated for 1 to 2 days to whole cell recording.

B. Measurement of Inhibition

Whole cell patch clamp experiments were performed using an Axopatch 200B amplifier (Axon Instruments, Burlingame, Calif.) linked to a personal computer equipped with pCLAMP software. The external and internal recording solutions contained, respectively, 5 mM BaCl$_2$, 10 mM MgCl$_2$, 10 mM HEPES, 40 mM TEACl, 10 mM glucose, 87.5 mM CsCl (pH 7.2) and 108 mM CsMS, 4 mM MgCl$_2$, 9 mM EGTA, 9 mM HEPES (pH 7.2). Currents were typically elicited from a holding potential of −80 mV to +10 mV using Clampex software (Axon Instruments). Typically, currents were first elicited with low frequency stimulation (0.067 Hz) and allowed to stabilize prior to application of the compounds. The compounds were then applied during the low frequency pulse trains for two to three minutes to assess tonic block, and subsequently the pulse frequency was increased to 0.2 Hz to assess frequency dependent block. Data were analyzed using Clampfit (Axon Instruments) and SigmaPlot 4.0 (Jandel Scientific).

Specific data obtained for N-type channels are shown in Table 2 below.

TABLE 2

N-type Calcium Channel Block

| Compound | IC$_{50}$ at 0.067 Hz (nM) | IC$_{50}$ at 0.2 Hz (nM) |
|---|---|---|
| P1 | 120 | 91 |
| P2 | 67 | 32 |
| P3 | 112 | 44 |
| P4 | 93 | 62 |
| P5 | 45 | 29 |
| P6 | 638 | 365 |
| P8 | 3000 | 987 |
| P9 | 1300 | 617 |
| P10 | 714 | 520 |
| P11 | 386 | 302 |
| P12 | 362 | 285 |
| P13 | 913 | 471 |

TABLE 2-continued

| | N-type Calcium Channel Block | |
|---|---|---|
| Compound | IC$_{50}$ at 0.067 Hz (nM) | IC$_{50}$ at 0.2 Hz (nM) |
| P14 | 366 | 252 |
| P15 | 287 | 216 |
| P16 | 1030 | 601 |

EXAMPLE 21

T-type Channel Blocking Activities of Various Invention Compounds

Standard patch-clamp techniques were employed to identify blockers of T-type currents. Briefly, previously described HEK cell lines stably expressing human α$_{1G}$ T-type channels were used for all the recordings (passage #: 4-20, 37° C., 5% $CO_2$). To obtain T-type currents, plastic dishes containing semi-confluent cells were positioned on the stage of a ZEISS AXIOVERT S100 microscope after replacing the culture medium with external solution (Table 3). Whole-cell patches were obtained using pipettes (borosilicate glass with filament, O.D.: 1.5 mm, I.D.: 0.86 mm, 10 cm length), fabricated on a SUTTER P-97 puller with resistance values of ~5 MΩ (Table 4).

TABLE 3

| External Solution 500 ml-pH 7.4, 265.5 mOsm | | | |
|---|---|---|---|
| Salt | Final mM | Stock M | Final ml |
| CsCl | 132 | 1 | 66 |
| CaCl$_2$ | 2 | 1 | 1 |
| MgCl$_2$ | 1 | 1 | 0.5 |
| HEPES | 10 | 0.5 | 10 |
| glucose | 10 | — | 0.9 grams |

TABLE 4

| Internal Solution 50 ml-pH 7.3 with CsOH, 270 mOsm | | | |
|---|---|---|---|
| Salt | Final mM | Stock M | Final ml |
| Cs-Methanesulfonate | 108 | — | 1.231 gr/50 ml |
| MgCl$_2$ | 2 | 1 | 0.1 |
| HEPES | 10 | 0.5 | 1 |
| EGTA-Cs | 11 | 0.25 | 2.2 |
| ATP | 2 | 0.2 | 0.025 (1 aliquot/2.5 ml) |

T-type currents were reliably obtained by using two voltage protocols: "non-inactivating", and "inactivation". In the non-inactivating protocol, the holding potential is set at −110 mV and with a pre-pulse at −100 mV for 1 second prior to the test pulse at −40 mV for 50 ms. In the inactivation protocol, the pre-pulse is at approximately −85 mV for 1 second, which inactivates about $^{15}$% of the T-type channels.

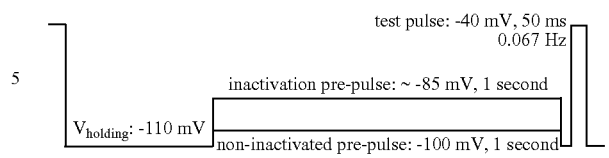

Test compounds were dissolved in external solution, 0.1-0.01% DMSO. After ~10 min rest, they were applied by gravity close to the cell using a WPI microfil tubing. The "non-inactivated" pre-pulse was used to examine the resting block of a compound. The "inactivated" protocol was employed to study voltage-dependent block. However, the initial data shown below were mainly obtained using the non-inactivated protocol only. IC$_{50}$ values are shown for various compounds of the invention in Table 5.

TABLE 5

| | Block of α$_{1G}$ T-type Channels | |
|---|---|---|
| Compound | IC$_{50}$ at −100 mV (nM) | IC$_{50}$ at −80 mV (nM) |
| P1 | Not tested | 8 |
| P2 | 117 | 51 |
| P3 | 910 | 364 |
| P4 | 230 | 390 |
| P5 | 73 | 13 |
| P6 | 1160 | 455 |
| P8 | No block | No block |
| P9 | 150-4500 | 160-2400 |
| P10 | 3460 | 882 |
| P11 | 1800 | 374 |
| P12 | 647 | 335 |
| P13 | 5000 | 488 |
| P14 | 609 | 99 |
| P15 | 692 | 115 |
| P16 | 2200 | 926 |

EXAMPLE 22

Activity of Invention Compounds in Formalin-Induced Pain Model

The effects of intrathecally delivered compounds of the invention on the rat formalin model were measured. The compounds were reconstituted to stock solutions of approximately 10 mg/ml in propylene glycol. Eight Holtsman male rats of 275-375 g size were randomly selected per test article.

The following study groups in Table 6 were used, with test article, vehicle control (propylene glycol) and saline delivered intraperitoneally (IP):

TABLE 6

| Formalin Model Dose Groups | | | |
|---|---|---|---|
| Test/Control Article | Dose | Route | Rat Number |
| Compound | 30 mg/kg | IP | 6 |
| Propylene glycol | N/A | IP | 4 |
| Saline | N/A | IP | 7 |

N/A = Not Applicable

Prior to initiation of drug delivery, baseline behavioral and testing data were taken. At selected times after infusion of the Test/Control Article, these data were again collected.

On the morning of testing, a small metal band (0.5 g) was loosely placed around the right hind paw. The rat was placed in a cylindrical Plexiglas chamber for adaptation a minimum of 30 minutes. Test Article or Vehicle Control Article was administered 10 minutes prior to formalin injection (50 µl of 5% formalin) into the dorsal surface of the right hindpaw of the rat. The animal was then placed into the chamber of the automated formalin apparatus where movement of the formalin injected paw was monitored and the number of paw flinches tallied by minute over the next 60 minutes (Malmberg, A. B., supra).

Results are presented as Maximum Possible Effect±SEM, where saline control=100% (Table 7)

TABLE 7

Efficacy of Invention Compounds in Formalin-Induced Pain Model

| Compound | Phase I | Phase II | Phase IIA |
| --- | --- | --- | --- |
| P1 | 94 ± 11 | 79 ± 14 | 72 ± 16 |
| P2 | 70 ± 8 | 82 ± 9 | 71 ± 12 |
| P4 | 50 ± 10 | 51 ± 10 | 42 ± 13 |
| P5 | 88 ± 13 | 62 ± 4 | 47 ± 5 |

It is understood that the foregoing detailed description and accompanying examples are merely illustrative, and are not to be taken as, limitations upon the scope of the invention. Various changes and modifications to the disclosed embodiments will be apparent to those skilled in the art. Such changes and modifications, including without limitation those relating to the chemical structures, substituents, derivatives, intermediates, syntheses, formulations and/or methods of use of the invention, may be made without departing from the spirit and scope thereof. U.S. patents and publications referenced herein are incorporated by reference.

The invention claimed is:

1. A compound of the formula

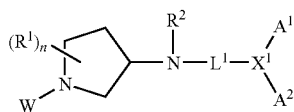

(1)

or the salts thereof, including all stereoisomeric forms thereof, wherein:
  $X^1$ is $CR^3$ or N;
  W is $L^2$-$A^3$ or $X^1(A^1)(A^2)$;
  each of $L^1$ and $L^2$ is a $C_1$-$C_{10}$ optionally substituted alkylene or $C_2$-$C_{10}$ optionally substituted alkenylene, wherein one or more said C is optionally replaced by a heteroatom selected from N, O or S, or further substituted with =O, or both;
  each of $A^1$, $A^2$ and $A^3$ is independently an optionally substituted 5-, 6- or 7-membered aliphatic or aromatic ring, and optionally fused to an additional aliphatic or aromatic ring;
  each $R^1$ is an optionally substituted alkyl (1-10C), alkenyl (2-10C), or alkynyl (2-10C), each optionally having one or more C, generally 1-4C, replaced by heteroatoms (N, O and/or S), or $R^1$ may be selected from aryl (5-12 ring members), arylalkyl (7-16C), and arylalkenyl (7-16C);
  $R^2$ is H or an optionally substituted alkyl (1-10C), alkenyl (2-10C), or alkynyl (2-10C), each optionally having one or more C, generally 1-4C, replaced by heteroatoms (N, O and/or S), or $R^2$ may be selected from aryl (5-12 ring members), arylalkyl (7-16C), and arylalkenyl (7-16C); and
  $R^3$ is H or an optionally substituted alkyl (1-10C), alkenyl (2-10C), or alkynyl (2-10C), each optionally having one or more C, generally 1-4C, replaced by heteroatoms (N, O and/or S), or $R^1$ and $R^2$ may be selected from aryl (5-12 ring members), arylalkyl (7-16C), and arylalkenyl (7-16C);
  n is 0-7;
  with the proviso that if $L^1$ is less than three linking atoms, $R^2$ cannot be hydrogen or $L^1$ must contain a C=O if $R^2$ is hydrogen;
  and with the further proviso that $L^1$ must contain at least three linking atoms if W is $L^2$-$A^3$.

2. The compound of claim 1, wherein $R^1$ is $C_1$-$C_6$ alkyl, $C_2$-$C_6$ alkenyl, or $C_2$-$C_6$ alkynyl, each optionally substituted, and optionally containing one or more heteroatoms selected from O, N and S, or $R^1$ is an inorganic substituent, or two $R^1$ form =O or =NOH, and n is 0-3.

3. The compound of claim 1, wherein said $R^1$ is halo, $NO_2$, $SO_2$, SO, NO, =O, =NOH, or COOR wherein R is H or $C_1$-$C_6$ alkyl.

4. The compound of claim 1, wherein $R^2$ is H, lower alkyl or lower alkenyl.

5. The compound of claim 4, wherein $R^2$ is H or methyl.

6. The compound of claim 1, wherein $L^1$ is $C_1$-$C_8$ alkylene or $C_1$-$C_8$ alkenylene, optionally substituted by =O.

7. The compound of claim 1, wherein $L^1$ is substituted by =O.

8. The compound of claim 7, wherein said =O is adjacent to $NR^2$ in formula 1.

9. The compound of claim 1, wherein each of $A^1$, $A^2$ and $A^3$ is independently optionally substituted phenyl, cyclohexyl.

10. The compound of claim 9, wherein said each of $A^1$, $A^2$ and $A^3$ is substituted with a halo, alkoxy or alkyl.

11. The compound of claim 9, wherein each of $A^1$, $A^2$ and $A^3$ is independently phenyl or cyclohexyl.

12. The compound of claim 11, each of $A^1$, $A^2$ and $A^3$ is phenyl, optionally substituted with a halogen.

13. The compound of claim 1, wherein W is $L^2$-$A^3$, and $A^3$ is phenyl or cyclohexyl, each optionally substituted with one or more substituents.

14. The compound of claim 13, wherein $A^3$ is phenyl or pyridyl optionally substituted with a halo, alkoxy or alkyl.

15. The compound of claim 1, selected from the group consisting of (R)-6,6-Bis(4-fluoro-phenyl)-hexanoic acid [1-(3,5-di-tert-butyl-4-methoxy-benzoyl)-pyrrolidin-3-yl]-methyl-amide;
  (R)-N-(1-Benzhydryl-pyrrolidin-3-yl)-N-methyl-3,3-diphenyl-propionamide;
  (S)-6,6-Bis-(4-fluoro-phenyl)-hexanoic acid[1-(3,5-di-tert-butyl-4-methoxy-benzoyl)-pyrrolidin-3-yl]-methyl-amide;
  (S)-N-(1-Benzhydryl-pyrrolidin-3-yl)-N-methyl-3,3-diphenyl-propionamide;
  (S)-N-(1-Benzhydryl-pyrrolidin-3-yl)-2-diphenylamino-N-methyl-acetamide;
  (S)-2-[(1-Benzhydryl-pyrrolidin-3-yl)-methyl-amino]-N,N-diphenyl-acetamide;
  (S)-3-Benzhydryl-1-(1-benzhydryl-pyrrolidin-3-yl)-1-methyl-urea;
  (R)-[6,6-Bis-(4-fluoro-phenyl)-hexyl]-[1-(3,5-di-tert-butyl-4-methoxy-benzoyl)-pyrrolidin-3-yl]-methyl-amine;

(S)-[6,6-Bis-(4-fluoro-phenyl)-hexyl]-[1-(3,5-di-tert-butyl-4-methoxy-benzoyl)-pyrrolidin-3-yl]-methyl-amine;
(R)—N-{1-[(4-Chloro-phenyl)-phenyl-methyl]-pyrrolidin-3-yl}-N-methyl-3,3-diphenyl-propionamide;
(S)—N-{1-[(4-Chloro-phenyl)-phenyl-methyl]-pyrrolidin-3-yl}-N-methyl-3,3-diphenyl-propionamide;
(R)-N-{1-[(3-Chloro-phenyl)-phenyl-methyl]-pyrrolidin-3-yl}-N-methyl-3,3-diphenyl-propionamide;
(S)-N-{1-[(3-Chloro-phenyl)-phenyl-methyl]-pyrrolidin-3-yl}-N-methyl-3,3-diphenyl-propionamide;
(R)-N-{1-[(2-Chloro-phenyl)-phenyl-methyl]-pyrrolidin-3-yl}-N-methyl-3,3-diphenyl-propionamide;
(S)-N-{1-[(2-Chloro-phenyl)-phenyl-methyl]-pyrrolidin-3-yl}-N-methyl-3,3-diphenyl-propionamide;
(R)-6,6-Bis-(4-fluoro-phenyl)-hexanoic acid[1-(3,5-di-tert-butyl-benzoyl)-pyrrolidin-3-yl]-methyl-amide;
(S)-6,6-Bis-(4-fluoro-phenyl)-hexanoic acid[1-(3,5-di-tert-butyl-benzoyl)-pyrrolidin-3-yl]-methyl-amide;
(R)-6,6-Bis-(4-fluoro-phenyl)-hexanoic acid[1-(4-tert-butyl-benzoyl)-pyrrolidin-3-yl]-methyl-amide;
(S)-6,6-Bis-(4-fluoro-phenyl)-hexanoic acid[1-(4-tert-butyl-benzoyl)-pyrrolidin-3-yl]-methyl-amide;
4-[6,6-Bis-(4-fluoro-phenyl)-hexanoylamino]-1-(3,5-di-tert-butyl-4-methoxy-benzoyl)-pyrrolidine-2-carboxylic acid ethyl ester;
4-[6,6-Bis-(4-fluoro-phenyl)-hexanoylamino]-1-(3,5-di-tert-butyl-4-methoxy-benzoyl)-pyrrolidine-2-carboxylic acid;
1-Benzhydryl-4-(3,3-diphenyl-propionylamino)-pyrrolidine-2-carboxylic acid ethyl ester;
1-Benzhydryl-4-(3,3-diphenyl-propionylamino)-pyrrolidine-2-carboxylic acid;
N-(1-Benzhydryl-2-oxo-pyrrolidin-3-yl)-3,3-diphenyl-propionamide;
1-Benzhydryl-3-(1-benzhydryl-2-oxo-pyrrolidin-3-yl)-urea;
N-(1-Benzhydryl-2-oxo-pyrrolidin-3-yl)-2-diphenylamino-acetamide; and
2-(1-Benzhydryl-2-oxo-pyrrolidin-3-ylamino)-N,N-diphenyl-acetamide.

16. A pharmaceutical composition comprising a compound of claim 1 and a pharmaceutically acceptable excipient.

17. A pharmaceutical composition comprising a compound of claim 15 and a pharmaceutically acceptable excipient.

18. The compound of claim 1, wherein $L^1$ is an alkylene or alkenylene chain having 3-6 members.

19. The compound of claim 18, wherein $L^1$ is substituted with =O at the carbon adjacent N.

20. The compound of claim 1, wherein $L^2$ is an alkylene or alkenylene having 1-4 members.

* * * * *